United States Patent [19]

Young et al.

[11] Patent Number: 5,017,789

[45] Date of Patent: May 21, 1991

[54] RASTER SCAN CONTROL SYSTEM FOR A CHARGED-PARTICLE BEAM

[75] Inventors: Phillip E. Young; David B. McColl, both of Albuquerque, N. Mex.

[73] Assignee: Loma Linda University Medical Center, Loma Linda, Calif.

[21] Appl. No.: 332,284

[22] Filed: Mar. 31, 1989

[51] Int. Cl.⁵ .......................... H01J 3/14; G01K 1/08
[52] U.S. Cl. .............................. 250/396 ML; 250/397; 250/398
[58] Field of Search ........... 250/396 R, 396 ML, 397, 250/398; 378/137; 313/361.1

[56] References Cited

U.S. PATENT DOCUMENTS

| | | | |
|---|---|---|---|
| 4,198,565 | 4/1980 | Ono | 250/396 ML |
| 4,380,703 | 4/1983 | Schmitt | 250/397 |
| 4,705,955 | 11/1987 | Mileikowsky | 250/491.1 |
| 4,812,658 | 3/1989 | Koehler | 250/396 ML |
| 4,845,370 | 7/1989 | Thompson et al. | 250/397 |

*Primary Examiner*—Bruce C. Anderson
*Attorney, Agent, or Firm*—Robert R. Meads

[57] ABSTRACT

A raster scan control system (18) for use with a charged-particle beam delivery system (20) provides precise control of large currents driving an inductive load. The beam delivery system includes a nozzle through which a charged-particle beam (24), such as a proton beam, passes prior to being directed to a target (32). The nozzle includes both fast and slow sweep scan electromagnets (204, 208) that cooperate to generate a sweeping magnetic field that steers the beam along a desired raster scan pattern at the target. The electromagnets are driven by large currents (213, 215) from the raster scan control system. The raster scan control system includes both fast and slow power amplifiers (212, 214) for delivering the desired large currents to the fast and slow electromagnets, respectively; monitoring means (206, 210) for monitoring the magnetic fields; sensing means (212, 230) for sensing the large currents; feedback means for maintaining the magnetic fields and large current at desired levels; out of tolerance means for automatically causing the servo power amplifiers to steer the beam away from the target area in the event the error signal becomes excessive; a programmable raster generator (80) for providing the fast and slow power amplifiers with a raster scan signal (216, 218) that defines the desired raster pattern; and a power supply (74) for delivering the requisite power to the power amplifiers and other components.

16 Claims, 12 Drawing Sheets

RASTER SCAN CONTROL SYSTEM FOR A CHARGED-PARTICLE BEAM

BACKGROUND OF THE INVENTION

The present invention relates to a magnetic field control system. More particularly, the present invention relates to a control system for controlling the magnetic fields created by the electromagnets in the nozzle of a charged-particle beam delivery system for the purpose of steering the charged-particle beam to follow a desired raster scan pattern across a selected target site.

A beam delivery system typically includes a nozzle through which a charged-particle beam, such as a proton beam, passes on its way to a target area. The nozzle usually includes collimator devices for confining the beam to a desired area or shape on the target. It is known in the art to include an electromagnet(s) in the nozzle that, as controlled by a drive current, generates a magnetic field that interacts with the charged-particle beam so as to bend or deflect the beam in a desired direction(s). By applying a current of a known magnitude to the electromagnet(s) in the nozzle, a magnetic field of a predictable intensity is generated that bends or deflects the beam a predictable amount. The stronger the magnetic field, the more the charged-particle beam can be bent. Hence, by selectively applying a current of a controlled magnitude to the electromagnet(s), the beam can be steered to a desired point on the target area.

The strength of the magnetic field required to bend a charged-particle beam dictates that an electromagnet having a large number of ampere-turns be employed. A low number of turns provides low resistance and inductance, but dictates that a high current be used. Unfortunately, such high currents are difficult to generate and control, and further create heat dissipation problems. A high number of turns advantageously allows the current to be maintained at a manageable level, but unfortunately brings with it a high inductance and resistance. Disadvantageously, a high inductance limits the rate at which the current, and hence the magnetic field, can change. Thus, prior art uses of electromagnets to steer a charged-particle beam have typically been limited to static uses, that is, uses where the steering of the beam is not changing, or is changing at a very slow rate. However, what is needed for a beam delivery system where the target is larger than the beam diameter is a system for dynamically steering a charged-particle beam so that the beam can be scanned across the target in a desired manner.

It is known in the art to use two magnets in the nozzle of a beam delivery system, oriented so as to create orthogonal magnetic fields, and to apply a fixed magnitude voltage to the coil of one magnet in one direction for a prescribed period of time, and then to apply this fixed magnitude voltage to the same coil in the opposite direction for a prescribed period of time, with the rate of change of the current being limited by the inductance of the coil. In this manner, a sawtooth current waveform is passed through the magnet coil, resulting in a magnetic field that linearly changes from one peak value to an opposite peak value. The changing magnetic field causes the beam to bend or move across the target area from one edge to the other in a straight line. When a similar fixed magnitude voltage is applied to the other magnet coil, another magnetic field, substantially independent of the first magnetic field, causes the beam to bend or move across the target area in a direction that is orthogonal to the movement caused by the first magnetic field. The combined effect of both magnetic fields is to move the beam across the target area in a diagonal sweep pattern. Typically, one magnet sweeps the beam in one direction, e.g. a horizontal direction, at a much faster rate than the other magnet sweeps the beam in an orthogonal direction, e.g., a vertical direction. Hence, one magnet is referred to as the "fast magnet" and the other is referred to as the "slow magnet".

Unfortunately, such a diagonal sweep pattern, even when there is a large difference between the sweep rates of the fast and slow magnets, does not always efficiently or uniformly cover the target area, there being significant portions of the target area that are not covered by a diagonal sweep pattern. Further, because of the large current magnitudes involved in such an arrangement, there is no easy way to control the current, especially at high sweep rates, other than to change its direction through the coil by abruptly reversing the voltage applied to the coil. This type of abrupt switching, or "bang-bang" type of control, makes it difficult to accurately control that portion of the target area that is swept with the beam. Either the beam sweep is on, in which case the diagonal sweep pattern goes from one edge of the target area all the way over to the other, or the beam sweep is off, in which case the beam does not move within the target area. What is needed, therefore, is a means for selectively controlling the sweep pattern within the target area so that all or a selected portion of the target area can be efficiently and uniformly swept with a beam that is accurately controlled.

SUMMARY OF THE INVENTION

The present invention provides a raster scan control system for use with a proton (or other charged-particle) beam delivery system that addresses the above and other needs. In general, the present invention provides a control system that allows for the precise control of magnetic fields, including control of the large currents driving an inductive load, such as the fast and slow electromagnets of a beam delivery system. More particularly, the present invention provides for a raster scan control system designed for use in a proton (or other charged-particle) beam delivery system that precisely controls the magnetic fields that are created by the fast and slow magnets of the beam delivery nozzle.

The raster scan control system of the present invention advantageously includes both fast and slow power drive circuits that generate and deliver the large currents needed by the fast and slow electromagnets, respectively, in order to generate the desired magnetic fields that sweep the charged-particle beam in a desired pattern. These power drive circuits are configured to generate the needed large output currents as controlled by a low level raster scan control signal applied thereto. The low level raster scan control signal is generated, in turn, by an appropriate control circuit, which control circuit may advantageously be programmed to produce whatever type of raster signals are required to steer the charged-particle beam efficiently and uniformly over the entire target area. A particular advantage of using a low level raster signal in this manner is that the target area need not have a uniform shape, such as a rectangle, as is common in the prior art with "bang-bang" type raster control circuits. Rather, the target can be any shape, even very irregular shapes.

Further, the raster scan system of the present invention, unlike any known prior art raster scan systems, advantageously includes monitoring means for monitoring both the currents and the magnetic fields created by the currents applied to the electromagnets. In one embodiment, the monitored current values are compared to desired values, and the difference between the monitored and desired values is applied back to the input of the power drive circuits as an error signal in order to appropriately adjust the current, and hence the magnetic field, in a direction that minimizes the error. In another embodiment, the monitored current values and/or the magnetic field values are selectively compared to desired values, with the difference being used as an error signal in order to adjust the magnetic field in a direction that minimizes the error. In either embodiment, the magnetic fields are precisely controlled, resulting in a beam that is steered by the magnetic fields so as to follow a desired raster scan pattern with little or no error.

Moreover, as a safety precaution, the raster scan system of the present invention includes means for automatically steering the charged-particle beam safely away from the target area to a shield or absorption device, such as the edge of a collimator included within the nozzle, in the event the magnetic field error signal becomes excessive, or in the event other problems are encountered, or during other energized but non-sweeping states of the system. This feature assures that the target area, typically a tumor within a patient, is safely protected from improper exposure to the charged-particle beam.

The present invention thus comprises a raster scan control system for a beam delivery system, where the beam delivery system includes means for generating a charged-particle beam and directing the beam through a nozzle towards a desired target. The raster scan control system includes at least one electromagnet positioned within the nozzle, the electromagnet having an electrical coil, and the electromagnet being oriented so as to create a magnetic field perpendicular to the beam when an electrical current is applied to the coil. According to well known principles, the magnetic field has a polarity and magnitude proportional to the polarity and amplitude of the electrical current applied to the coil. The magnetic field interacts with the beam as the beam passes through the nozzle so as to bend or deflect the beam by an amount determined by the magnitude of the magnetic field. The beam may thus be steered or guided as it passes through the nozzle by selectively controlling the amplitude and polarity of the current applied to the coil. The raster scan control system also includes: (a) means for generating the electrical current that is applied to the coil of the electromagnet, this electrical current having a specified waveform that defines its magnitude and polarity as a function of time; (b) means for monitoring the magnitude of the current applied to the coil of the electromagnet and/or the magnitude of the magnetic field created when the current is applied to the coil of the electromagnet; and (c) feedback means coupled to the monitoring means and the electrical current generating means for automatically comparing the monitored value of the current or magnetic field to a desired value and for adjusting the magnitude of the electrical current in a direction that minimizes the difference between the monitored value and the desired value. Advantageously such a raster scan control system allows the desired value of the magnetic field to be automatically maintained.

The present invention further includes a system for scanning a target area with a charged-particle beam. The system includes: (1) means for generating a charged-particle beam having a desired energy; (2) means for directing the beam through a pair of magnets having orthogonally oriented magnetic fields; (3) means for generating a sweeping magnetic field with a first of the pair of magnets, the sweeping magnetic field causing the beam to sweep back and forth across the target area in one direction; (4) means for generating a stair-stepped magnetic field with a second of the pair of magnets, the stair-stepped magnetic field assuming a first magnetic field strength for a first prescribed period of time, a second magnetic field strength for a second prescribed period of time, a third magnetic field strength for a third prescribed period of time, and so on up to an nth magnetic field strength for an nth prescribed period of time, where n is an integer and represents the number of steps in the stair-stepped magnetic field, the stair-stepped magnetic field causing the beam to step across the target area in a direction orthogonal to the direction caused by the sweeping magnetic field; and (5) means for synchronizing the sweeping magnetic field generating means with the stair-stepped magnetic field generating means so that the sweeping magnetic field begins its sweep coincident with the beginning of one of the prescribed periods of time during which the stair-stepped magnetic field assumes one of its n magnetic field strengths. The system combines the sweeping and stair-stepped magnetic fields in a manner that steers or directs the beam across the target area in a desired raster scan pattern. Advantageously, the prescribed periods of time associated with the stair-stepped magnetic field generating means may all be equal, in which case a generally rectangular-shaped target area will be swept; or they may be different, in which case irregular target shapes may be swept. Further, the second magnetic field can be programmed to repeat the n stair-stepped field strength levels during a single beam spill from the beam source so as to provide multiple scans of the target area. Such multiple scans provide a mechanism for controlling the dosage of the beam delivered to the target. Additional dosage control and enhanced dose uniformity on the target area may be achieved on successive repeats of the stair-stepped levels by following a scan down sweep with a scan up sweep, and by setting the scan up levels midway between the scan down levels.

The present invention may also be characterized as a raster magnet control system that includes: (1) a pair of magnets having orthogonally oriented magnetic fields, each magnet having a coil associated therewith; (2) means for passing a charged particle beam through first one and then the other of the magnetic fields, whereby the charged particle beam is deflected in one direction by the first of the magnetic fields, and in an orthogonal direction by the second of the magnetic fields; (3) means for dynamically controlling the magnitude of the magnetic fields, whereby the deflection of the charged particle beam may be dynamically steered in orthogonal directions; and (4) shutdown means for automatically preventing the charged particle beam from following a prescribed course through both of said magnets in the event certain conditions occur. The dynamic control means includes means for applying a drive current to each of the coils, the drive current producing a magnetic field having a magnitude proportional to the magnitude of the drive current; means for monitoring the magnitude of each of the drive currents and/or magnetic fields; and feedback means coupled to the monitoring means and the drive means for automatically adjusting the magnitude of each drive current in order to produce a specified magnetic field magnitude. Advantageously, this dynamic control means assures that the desired magnetic fields are dynamically maintained at all times, thereby assuring accurate dynamic control of the charged-particle beam as it passes through the magnetic fields.

Further, the present invention includes a method of scanning a target area with a charged-particle beam. The method includes the steps of: (a) generating a charged-particle beam having a desired energy; (b) directing the beam through a pair of magnets having orthogonally oriented magnetic fields, each magnet having a coil associated therewith; (c) generating a sweeping magnetic field with a first of the pair of magnets by energizing its coil with a first current having an amplitude that initially is increasing, to sweep the magnetic field in one direction, and subsequently is decreasing, to sweep the magnetic field in the other direction; (d) generating a stair-stepped magnetic field with a second of the pair of magnets by energizing its coil with a second current having a stair-stepped waveform, the stair-stepped waveform causing the second current to assume a first fixed value for a first prescribed period of time, stepping a prescribed amount to a second fixed value, assuming the second fixed value for a second prescribed period of time, and so on, the stair-stepped magnetic field causing the beam to step across the target area in a direction orthogonal to the sweep direction; and (e) synchronizing the delivery of the first and second currents to the coils of the first and second magnets so that the first current is increasing or decreasing in amplitude during those periods of time when the second current assumes one of the fixed values in its stair-stepped waveform.

It is a feature of the charged-particle raster scan control system described herein, in accordance with one embodiment thereof, that only one magnet will be changing its respective magnetic field at any given time. This advantageously allows for a smaller power supply to be used because the largest power requirements come from the inductive loads that exist only when a magnet is changing its current and magnetic field values.

It is a further feature of the present invention to provide a charged-particle raster scan control system wherein the raster scan pattern to be followed by the charged-particle beam on a target surface may be programmably controlled to efficiently and uniformly cover the entire area of a given target, including irregular shaped targets.

It is another feature of the invention to provide such a control system wherein the magnetic fields used to steer the charged particle beam are dynamically controlled, through the use of appropriate feedback signals, to ensure that the beam is being deflected or steered to follow a prescribed path.

It is yet another feature of the present invention to provide such a control system wherein safety features are included to rapidly and automatically prevent the beam from striking the target in the event certain out-of-tolerance conditions are sensed.

Still another feature of the present invention provides for the linking of the raster control system with other systems used in generating and delivering a charged-particle beam to a desired target, including control of the raster control system from a host computer, and the shutting down of the system from a remote site. In accordance with one embodiment, this feature is achieved by utilizing the raster control system as an embedded control system within a supervisory control system.

BRIEF DESCRIPTION OF THE DRAWINGS

The above and other features and advantages of the present invention will be more apparent from the following more particular description thereof, presented in conjunction with the following drawings wherein.

DETAILED DESCRIPTION OF THE INVENTION

The following description is of the best presently contemplated mode of carrying out the invention. This description is not to be taken in a limiting sense, but is made merely for the purpose of describing the general principles of the invention. The scope of the invention should be determined with reference to the appended claims.

Figure 1:
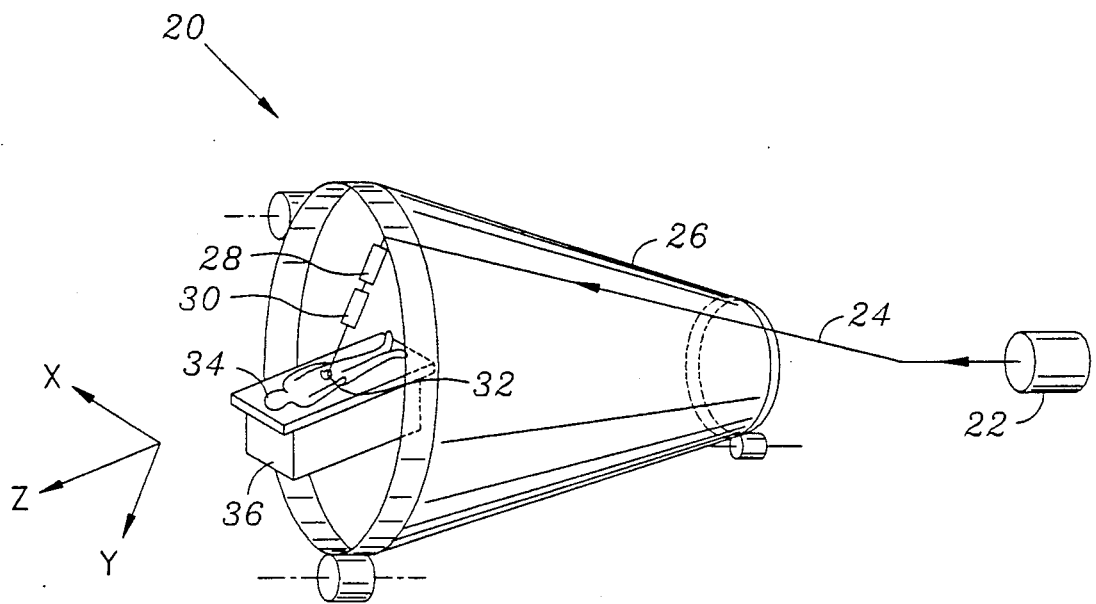
FIG. 1 is a simplified schematic representation of a charged-particle beam delivery system, and illustrates how such a system is used to irradiate a desired target area on a patient.

Referring first to FIG. 1, a simplified schematic representation of a charged particle beam delivery system 20 is shown. This system includes a source 22 of an accelerated charged particle beam that generates a beam 24 of charged-particles having a desired energy. The beam 24 is directed through a rotatable gantry 26 where it is directed, using conventional means, through a fast scan magnet 28 and a slow scan magnet 30. Typically, the fast scan magnet 28 and the slow scan magnet 30 are mounted in a suitable nozzle structure that also includes appropriate collimator devices used to confine the beam 24 to a desired target area 32. For medical applications, the target area 32 is generally a selected area on or in a patient 34, which patient is situated on a patient table 36. The patient table 36, as well as the gantry 26, may each be selectively rotated relative to each other in order to allow the beam 24 to strike the target area 32 from any desired angle and direction. It is the function of the beam delivery system 20 to present the charged particle beam 24 to the target area 32 in a manner that allows the beam to be swept across the entire target area so that the target area receives a specified pattern, usually uniform, of dosage of the beam. For this purpose, a coordinate system is defined, as shown in FIG. 1, wherein the Z axis is the patient's head-to-toe direction, the Y axis is into the patient along the beam, and the X axis is across the width of the patient perpendicular to the beam. It is to be understood that this coordinate system is for reference purposes only, and that other reference systems and coordinate systems could just as easily be employed.

Figure 2:
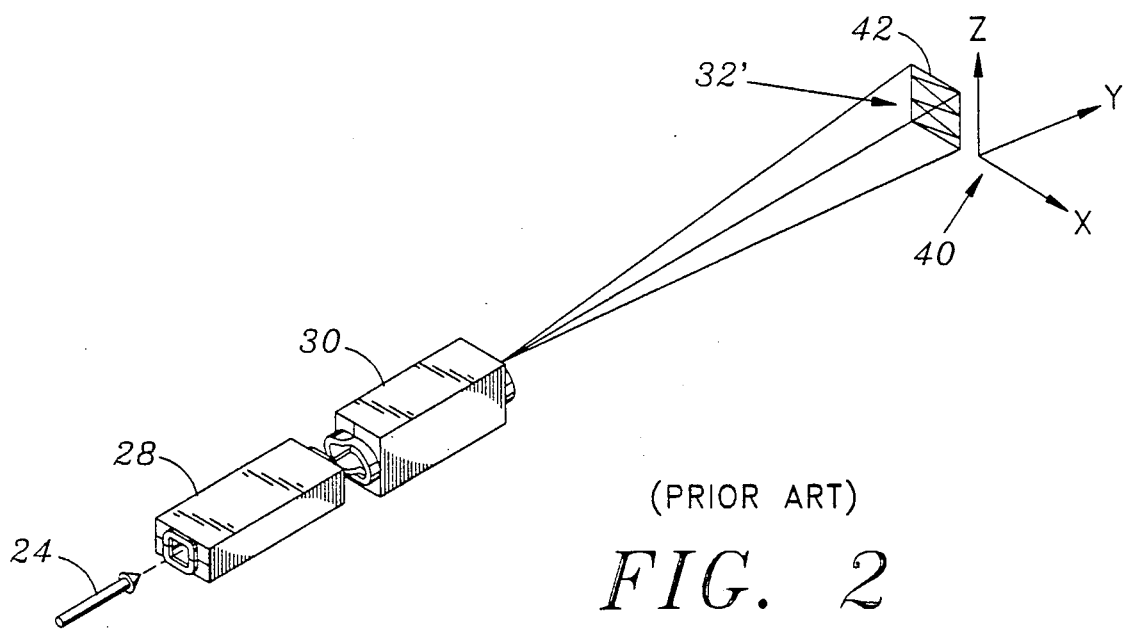
FIG. 2 is a schematic representation of the fast and slow magnets of a prior art raster scan system, and illustrates the diagonal sweep pattern resulting therefrom at a target site.

Referring next to FIG. 2, a schematic representation of the fast scanning magnet 28 and the slow scanning magnet 30, of a configuration used in the prior art, is illustrated. In such a system, the beam 24 enters the fast scanning magnet 28 upstream from the slow scanning magnet 30. It is the function of the fast scanning magnet 28 to create a magnetic field that deflects the beam in an X direction, using the coordinate system shown at 40. As seen in FIG. 2, this coordinate system, in general, places the X direction as a horizontal direction. Similarly, for the orientation shown in FIG. 2, the Z direction is a vertical direction. It is the function of the slow scanning magnet 30 to create a magnetic field that moves or scans the beam in a vertical or Z direction. The combination of the fast magnet 28 and the slow magnet 30 causes a diagonal sweep pattern 42 to be present on the target area 32. That is, as the fast scan magnet 28 moves the beam in an X direction, the slow scan magnet 30 is moving the beam in a Z direction, thereby resulting in the diagonal scan pattern 42 illustrated in FIG. 2.

Figure 3A:
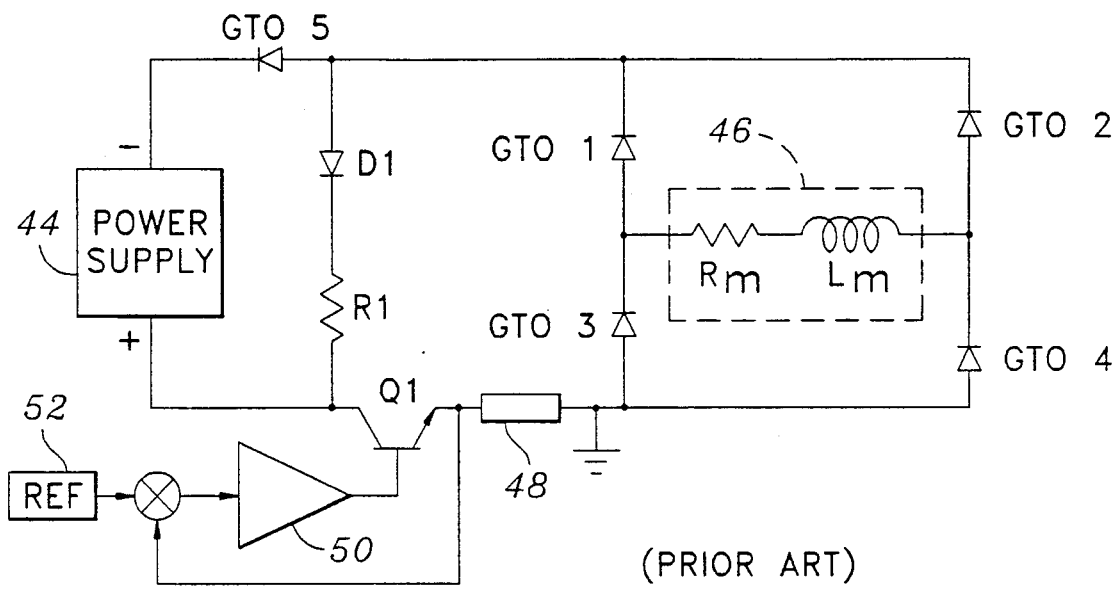
FIG. 3A is an electrical schematic diagram of a prior art power drive circuit used to control the fast scan magnet of the raster scan system of FIG. 2.

In order to better appreciate the differences between the present invention and the prior art, a brief description is next presented of the control circuits that are used in the prior art fast and slow scan system of FIG. 2. Referring first to FIG. 3A, a schematic diagram of the power drive circuit for the fast magnet 28 is shown. This circuit includes a single power supply 44 that is connected to a coil 46 of the fast magnet through a properly timed bridge network of gate turn-on thyristor (GTO) switches, GT01, GT02, GT03, and GT04. The firing sequence on these switches is as follows: To begin the horizontal scan deflection, GTO's 1, 4 and 5 are simultaneously turned on to apply a constant forcing voltage from the power supply 44 to the inductive load $L_m$. A current-controlled transistor Q1 helps to linearize this current. The amount of current flowing in the circuit is sensed by measuring the voltage across a shunt resistor 48. An amplifier 50 drives the base of transistor Q1 as controlled by a reference voltage 52 as compared with feedback signal representatives of the current flowing through the magnet load 46. As indicated, this feedback signal is obtained by measuring the voltage across the shunt resistor 48, which voltage is proportional to the current flowing therethrough according to Ohm's law. Returning to the firing sequence, GTO's 1, 4 and 5 are simultaneously turned on to apply a constant forcing voltage from the power supply 44 across the load 46. GTO's 2, 3 and 5 could alternatively be simultaneously turned on in order to start the scan in the opposite direction, which is achieved by having the current flow through the load 46 in the opposite direction. Because of the high inductance associated with the inductor $L_m$, the current flowing therethrough is not allowed to change rapidly. When the desired peak current is reached, GT05 is switched off, effectively isolating the power supply 44 from the load. This also causes the magnet voltage to reverse polarity and forces its current to decay toward zero in a linear fashion as dictated by the actuator Q1 and the diode resistor network comprising diode D1 and resistor R1. This diode resistor network is shunted across the series combination of GT05 and the power supply 44. The resistor R1 provides a substantial amount of power dissipation during the discharge cycle, thereby simplifying the power requirements of more expensive transistor actuators. When the magnet current reaches zero, GTO's 1 and 4 are turned off, and GTO's 2, 3 and 5 are turned on, thereby applying a forcing voltage of the opposite polarity to the magnet load 46, which repeats the above cycle for the opposite scan direction.

In the manner described above, an essentially triangular current wave form is passed through the magnet load 46. This triangular wave form peaks at a current value of one polarity and linearally ramps to a peak current value of the opposite polarity. Ideally, the maximum frequency of this triangular wave form is controlled by the switching frequency of the control signals applied to the GTO's. However, in practice the inductance value $L_m$, as well as the voltage and power ratings of the power supply, provide an upper limit as to how fast the current can ramp from one value to another.

Figure 3B:
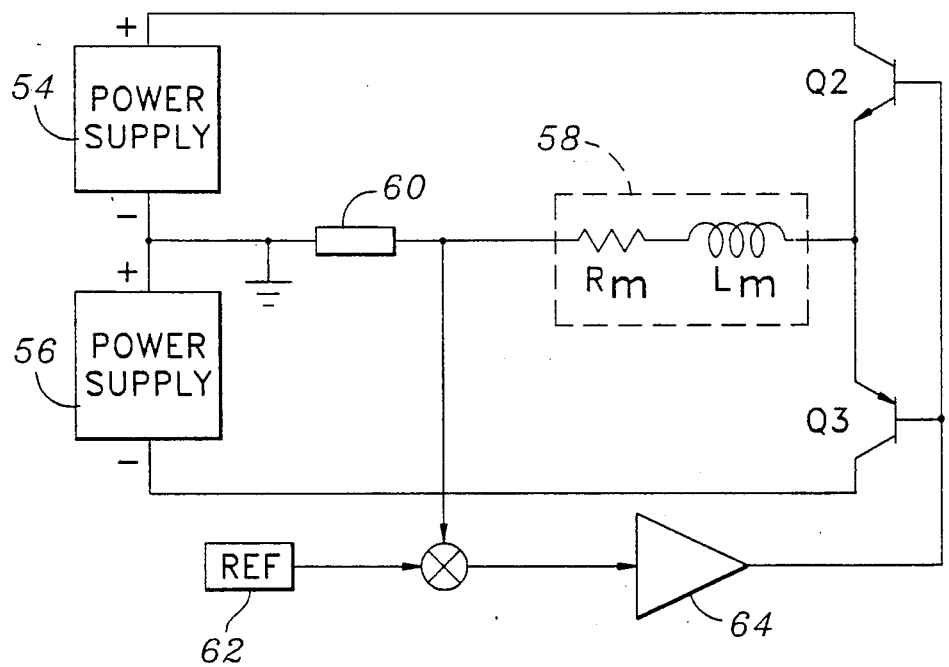
FIG. 3B is an electrical schematic diagram of a prior art power drive circuit used to control the slow scan magnet of the system of FIG. 2.

Referring next to FIG. 3B, the slow scan circuit is illustrated. Though the inductance of the vertical scanning magnet 30 is generally six times greater than the horizontal magnet, the ramping rate is 30 times slower, requiring a much lower forcing voltage and a greatly reduced reactive power requirement. At these power levels, it is more cost effective to use a less complex bi-polar design, employing a push-pull configuration. This configuration includes two power supplies 54 and 56, each connected to a transistor switch, Q2 or Q3. Further, a shunt resistor 60 is connected to the common leg of the circuit through which the current always flows. As seen in the figure, transistor Q2 is an NPN transistor; and transistor Q3 is a PNP transistor. The emitters of these two transistors are connected together and also connected to the magnet coil load 58 of the slow magnet 30. The other end of the magnet load 58 is connected to a shunt resistor 60 which, in turn, is connected to the tandem connection of the power supply 54 and the power supply 56. The voltage across the shunt resistor 60 is monitored and compared to a reference voltage 62, the difference being applied to a control amplifier 64, the output of which is connected to both bases of transistors Q2 and Q3. In operation, current of one direction is passed through the load 58 by energizing switch Q2, thereby having current flow clockwise through the loop comprising the load 58, the transistor Q2, the shunt resistor 60, and the power supply 54. To change current directions, transistor Q2 is turned off, and transistor Q3 is turned on, thereby having current flow counterclockwise throughout the loop comprising the power supply 56, the shunt resistor 60, the magnet load 58, and the transistor Q3.

Advantageously, the two prior art circuits described above in connection with FIGS. 3A and 3B, allow the beam 24 to be controlled in a relatively simple manner as it passes on its way to the target 42. Disadvantageously, the control is limited to a triangular scan pattern, because both the fast and slow scan circuits drive their respective magnet loads with a triangular current waveform (which triangular waveform results from swithing a large voltage across the mostly inductive load). As is evident from the representation of such a scan pattern shown in FIG. 2, much of the target area is missed by such a triangular scan pattern (there being a great deal of "white space" or areas not swept by the sweeping beam), thereby creating an uneven exposure of the target to the beam. While some applications may exist where an uneven exposure of the target to the charged-particle beam is acceptable, and even preferable, medical applications generally require as uniform of an exposure as possible. This is because in a medical application, the charged-particle beam is typically directed at a tumor or other malignant area where the beam is used to kill cancerous or malignant cells. An uneven exposure of the exposed area could therefore result in not all of the cells being killed, thereby reducing the effectiveness of the treatment.

Some techniques can be employed using the circuits of FIGS. 3A and 3B to improve the coverage of the target area, but even these techniques do not permit a uniform dose of the target area with the scanning beam. For example, it is possible to adjust the slow scan rate so not much distance is covered in the z direction for a complete cycle in the x direction, thereby creating a compressed scan pattern. However, even such a compressed scan pattern is soon limited by overlap (due to the finite width of the beam) at the ends of the horizontal sweep, which overlap disadvantageously results in an uneven exposure of the target. It is also possible to undertake additional scans of the target, with each scan beginning at a different starting point (so that a subsequent scan pattern does not fall directly on top of a prior scan pattern). However, even this multiple scan approach results in uneven exposure due to the areas of overlap where one scan pattern crosses the other. It is thus apparent that there is a need for a system that can efficiently cover the entire target area with an even exposure. Advantageously, the present invention addresses this need.

Figure 4:
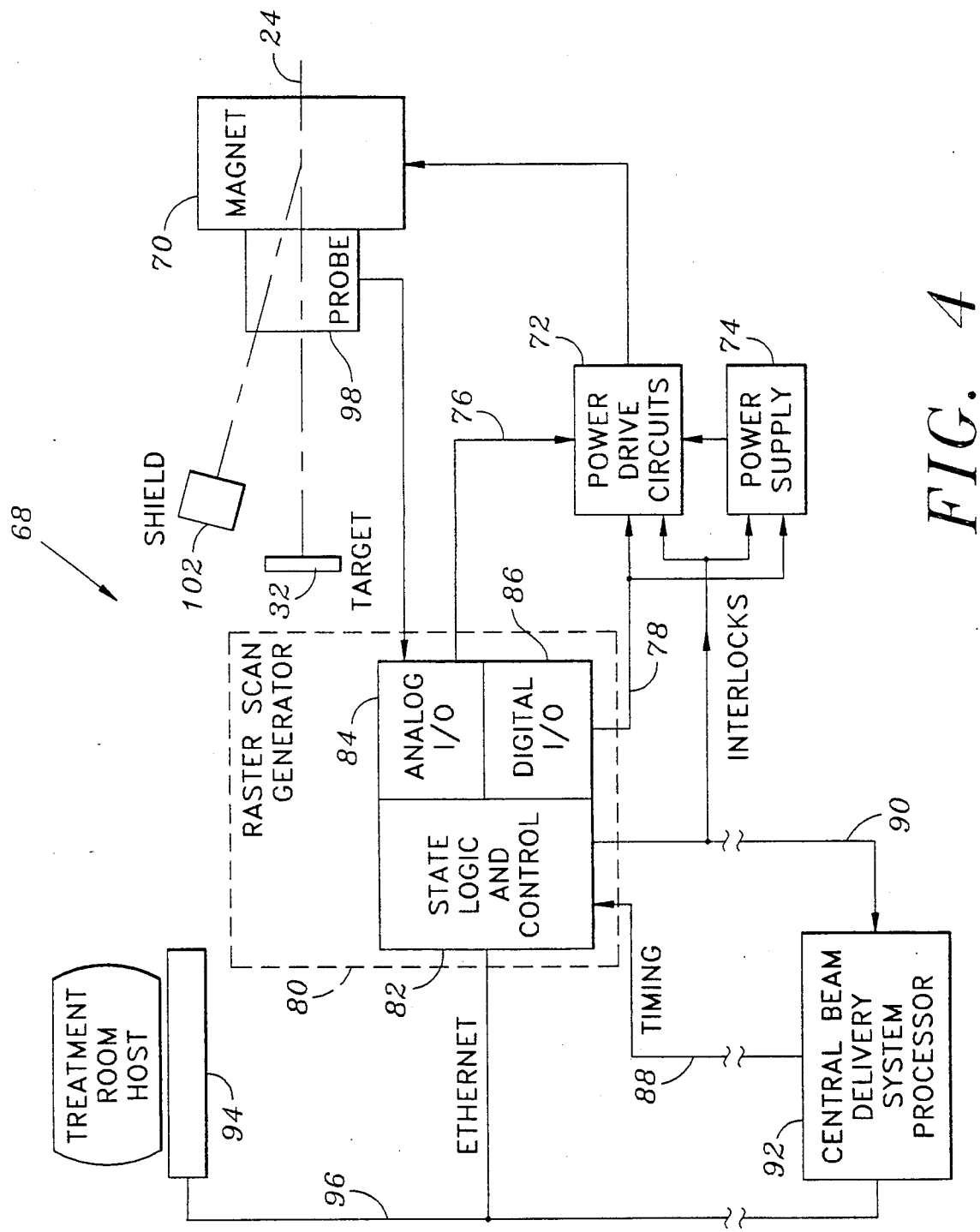
FIG. 4 is a block diagram illustrating the basic configuration of the raster scan control system of the present invention.

A block diagram of a raster scan system 68 in accordance with the present invention is illustrated in FIG. 4. The system 68 includes at least one magnet 70 through which the charged-particle beam 24, from a source 22 (FIG. 1) is passed on its way to a selected target 32. The magnet 70 is controlled with a power drive circuit 72. The drive circuit 72 obtains raw power from a power supply 74, and is controlled with both analog signals 76 and digital signals 78 obtained from a raster scan generator circuit 80. The raster scan generator includes state logic and control circuits 82, as well as analog input-/output (I/O) circuits 84, and digital I/O circuits 86. Significant timing signals 88 are obtained from a central processor 92, or other timing circuits, which processor 92 is used to coordinate the operation of the overall beam delivery system, and which processor may be located remote from the raster scan system. Interlock signals 90 generated by the raster scan generator 80, or elsewhere within the overall beam delivery system, are also sent to the main processor 92, as well as to the power drive circuits 72. Local control of the raster scan system is obtained from a treatment room host processor or computer 94, which processor 94 communicates with the raster scan generator 80 and the central beam delivery system processor 92 over a suitable communication network 96.

One principal advantage of the raster scan system 68 over any known prior art system is the capability of the system to monitor the strength of the magnetic field generated by the magnet 70 with a magnetic field probe 98. This probe 98 is emersed in the magnetic field through which the beam 24 passes. It generates a magnetic field strength signal 100 that may be sent to the analog I/O circuits 84 of the raster scan generator 80. (In one embodiment, described more fully below in connection with FIG. 12, this magnetic field strength signal may also be sent directly to the power drive circuit 72 and used as a closed-loop feedback signal.) If the probe signal 100 indicates that the magnetic field strength is out-of-tolerance in any way, a shutdown mechanism is immediately activated that stops delivery of the beam 24 to the target 32. This shutdown is accomplished in several ways. In the short term (i.e., within a few milliseconds), the power drive circuits create a magnetic field that diverts the beam from the target 32 to a suitable shield 102, where the beam is harmlessly absorbed. In the long term (i.e., within a few seconds) the source of the beam 24 may be turned off at the source 22 (FIG. 1) by the processor 92. However, because the beam source 22 may be a large complex device, e.g., such as a cyclotron (which cyclotron may have a significant start-up time period), shutting down of the beam at the source is generally reserved for major emergencies or for when the system is not in use. At other times, the beam 24 is simply diverted to an appropriate test target (not shown) or to the shield device 102 (or equivalent).

Figure 5:
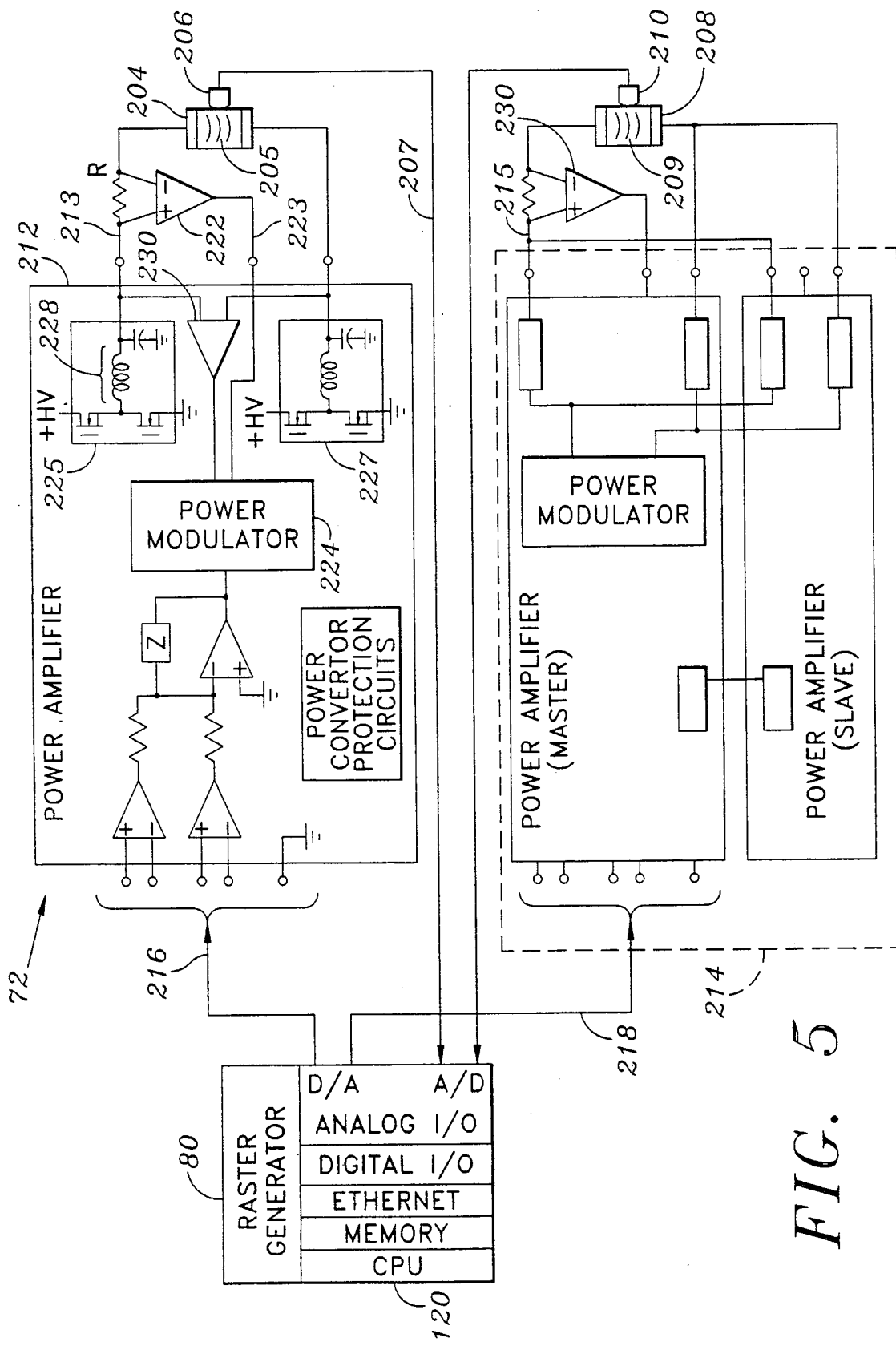
FIG. 5 is a more detailed block diagram of the raster scan control system of the present invention.

Turning next to FIG. 5, a more detailed block diagram of the preferred embodiment of the power drive circuits 72 of the raster scan system 68 of FIG. 4 is illustrated. As seen in FIG. 5, the preferred system includes a fast scan magnet (or "fast magnet") 204 and a slow scan magnet (or "slow magnet") 208, similar to the prior art (FIG. 2). Like the prior art devices, each magnet includes a magnet coil. When the magnet coil of each magnet is energized by an electrical current, a fast magnetic field 205 (fast magnet) and a slow magnetic field 209 (slow magnet) is generated. (These magnetic fields are represented in FIG. 5 by a series of radiating wavefront lines within their respective magnets.) Unlike the prior art, however, a fast magnetic field probe 206, and a slow magnetic field probe 210, sense the instantaneous strength of the respective magnetic fields 205 and 209. This sensing allows the drive circuits, as will be explained hereafter, to make adjustments in the electrical currents creating the magnetic fields so that the magnitudes and polarities of such magnetic fields can be corrected in the event that some error condition is sensed.

Further, unlike the prior art, each magnet 204 and 208 is driven by a power amplifier 212 and 214, respectively.

These power amplifiers generate the large currents 213 and 215 ("output currents") used to drive the fast magnet 204 and the slow magnet 208 as controlled by respective raster control signals 216 and 218, obtained from a digital-to-analog (D/A) portion 120 of the raster generator 80. (It is noted that in the description presented herein a signal may be referenced by a reference number that on the drawing is connected to the signal line on which the signal appears. It is to be understood that such reference numerals may refer to either the signal itself, or the signal line on which the signal appears.) These raster control signals 216 and 218 may be considered as the raw "input" signals to the power amplifier circuits 212 and 214, for it is these signals that define the desired current waveform that the large currents generated by the power amplifiers 212 and 214 are to take, and hence the waveform that the amplitude of the magnetic fields 205 and 209 are to follow.

The raw input signals 216 and 218 are modified, as necessary, in order to correct for any deficiencies that may exist in the magnetic fields 205 and 209. This modification is achieved using, in effect, separate current and magnetic feedback loops. The fast magnet feedback loop includes the magnetic probe 206, which probe 206 generates a signal 207 indicative of the instantaneous strength of the magnetic field 205; and a current monitor 222, which monitor generates a signal 223 indicative of the instantaneous magnitude of the current 213. The current signal 223 is connected to a pulse width modulator 224. It is the function of the pulse width modulator 224 to control internal drive circuits 225 and 227 in such a manner so as to generate the desired output current 213. The manner in which a pulse width modulator performs this function is well known in the art. Essentially, the pulse width modulator 224 pulses the front end of the internal drive circuits 225 and 227 on and off at a prescribed rate and duty cycle (pulse width). The pulsed output is filtered in an L-C filter 228 to produce an average current 213. The value of the current 213 is measured by current monitor 222 (an operational amplifier that measures the differential voltage across a sense resistor R through which the current 213 flows) and this value is fed back to the pulse width modulator 224 in order to adjust the pulse width (duty cycle) in an appropriate direction so as to cause the output current 213 to assume a desired value. Further, at the same time that drive circuit 225 is "pushing" current into the load (magnet) 204, the drive circuit 227 is "pulling" current from the load. If the current direction changes, then drive circuit 227 "pushes" and drive circuit 225 "pulls". Differential amplifier 230 monitors the voltage across the load (magnet) 204, and provides a further mechanism for adjusting the pulse width (duty cycle) of the modulator 224 as required in order to between the output voltage within desired limits.

The input signal 216 is also connected to the pulse width modulator 224 through a series of amplifiers internal to the power amplifier 212. The input signal controls the output current 213 by defining the value the current 213 should take at any given time. In other words, the input signal 216 functions as a reference signal against which the feedback signal 223 is compared to that adjustments can be made to minimize the difference, if any, between the reference current value and the measured output current value.

Advantageously, the power amplifier 212 for the fast scan magnet 204 may be realized using a commercially available device manufactured by Copley Controls Corporation of Newton, Mass., identified as the Model 290 Power Amplifier. The power amplifier 214 for the slow scan magnet 208 may be realized using two such Model 290 Power Amplifiers, connected in a master-slave configuration. Two such amplifiers are used for the slow scan circuits in order to increase the output capacity of the amplifier 214, thereby providing the higher current values needed by the slow scan magnet, while still utilizing a single feedback signal (connected to the master portion of the configuration). However, in all other respects, the slow scan master-slave power amplifier 214 operates the same as the fast scan amplifier 212, except that the input signal 218 specifies a different output current 215 for the slow scan magnet 208, as is explained more fully below.

It is a fundamental principle of electromagnetics that the magnetic field generated in an electromagnet, such as either the fast magnet 104 or the slow magnet 108, is directly proportional to the magnitude of the current applied to its coil. Thus, one might ask why it is necessary to monitor both the current and the magnetic field, as is done by the system of the present invention, when monitoring one or the other should be sufficient, as either should be proportional to the other. The answer is that, in practice, their may be some discrepancy between the current and magnetic field due to imperfections in the magnets, or due to variations in the performance of the magnets caused by environmental or other factors, or due to the inability of the sensing devices (magnetic or current) to always perform as designed. For example, current sensing and control alone will not detect a shorted magnet coil. Known prior art raster scan systems, such as are described in connection with FIGS. 3A and 3B, only attempt to monitor current (and even then, only on a limited basis), and the feedback schemes employed are not able to react very rapidly in correcting any deficiencies that are detected. In contrast, the present invention recognizes the advantage of directly monitoring the magnetic field, because it is the magnetic field that causes the actual deflection of the beam. While the current feedback scheme provides a feedback mechanism that reacts essentially instantaneously in correcting any deficiencies that are sensed, the magnetic feedback scheme provides protection against additional deficiencies that are not sensed by the current feedback. Further, the present invention provides a great deal of flexibility in the manner in which it can be used because, as explained more fully below, both the raster input signals 116 and 118 can be programmably controlled in any desired manner.

In the preferred embodiment, the inductance of the coil of the fast magnet 204 is about 4.9 mH and its resistance is approximately 30 milliohms. In contrast, the inductance of the coil of the slow magnet 208 is about 18.3 mH, approximately 3 times the inductance of the fast magnet coil, and its resistance is around 130 milliohms. The coils for the scanning magnets are preferably made from hollow copper tubing. Water cooling is used to remove the heat load from resistive and eddy current heating. The fast scanning magnet 204 is designed to produce from 21 to 22 gauss/amp; and the slow scanning magnet is designed to produce from 11.5 to 12.5 gauss/amp.

Figure 6A:
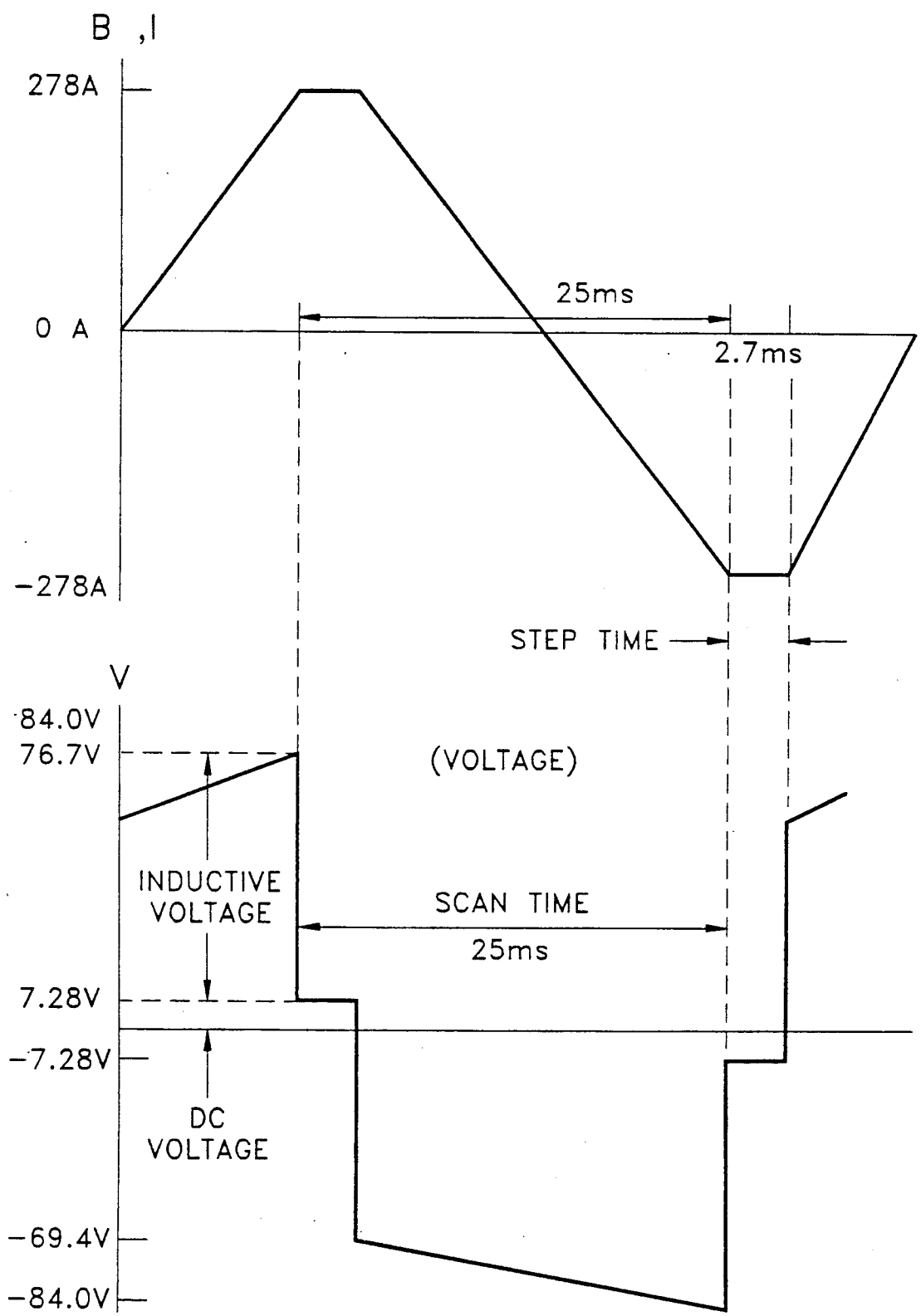
FIGS. 6A and 6B are current, magnetic, and voltage waveform diagrams for the fast and slow magnets, respectively, of FIG. 5.
Figure 6B:
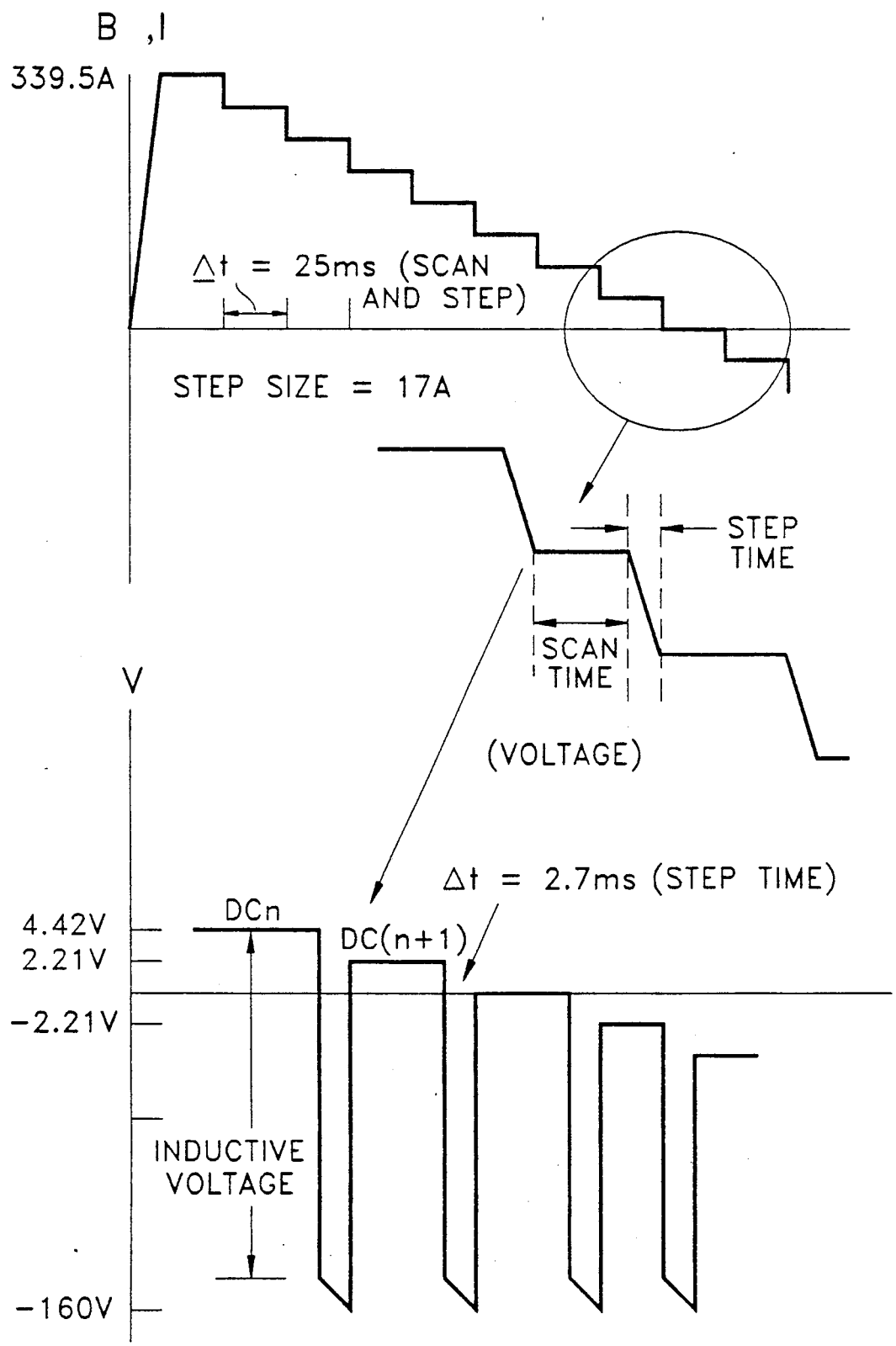

Again, in the preferred embodiment, the current 213 delivered to the fast magnet 204 has a peak value of around 305 amperes, and varies from one peak value to the next peak value at a rate of around 20 Hz (50 msec period). The current 215 delivered to the slow magnet 208, in contrast, has a peak value of around 432 amperes and steps down a specified increment, such as 17 amperes, every 25 msec. Representative voltage, current and magnetic field waveforms for the fast and slow magnets are illustrated in FIGS. 6A and 6B, respectively. It is to be emphasized that the values shown in FIGS. 6A and 6B are only exemplary, and that these values can be programmably changed as needed in order to best scan a particular target area. A typical scan time of 25 milliseconds, for example, is used for a ±25 cm field width with a step time of 3 milliseconds, and a slow current step size of 17 amps.

Figure 7A:
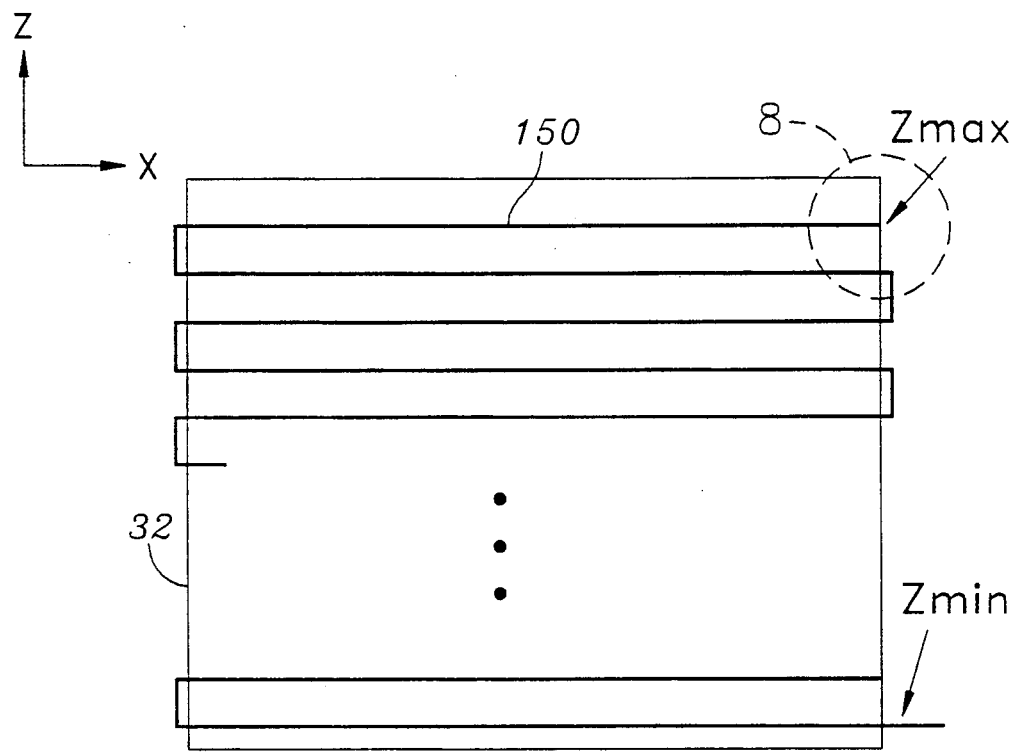
FIGS. 7A and 7B illustrate representative raster scan patterns that may be achieved using the raster scan system of the present invention.
Figure 8:
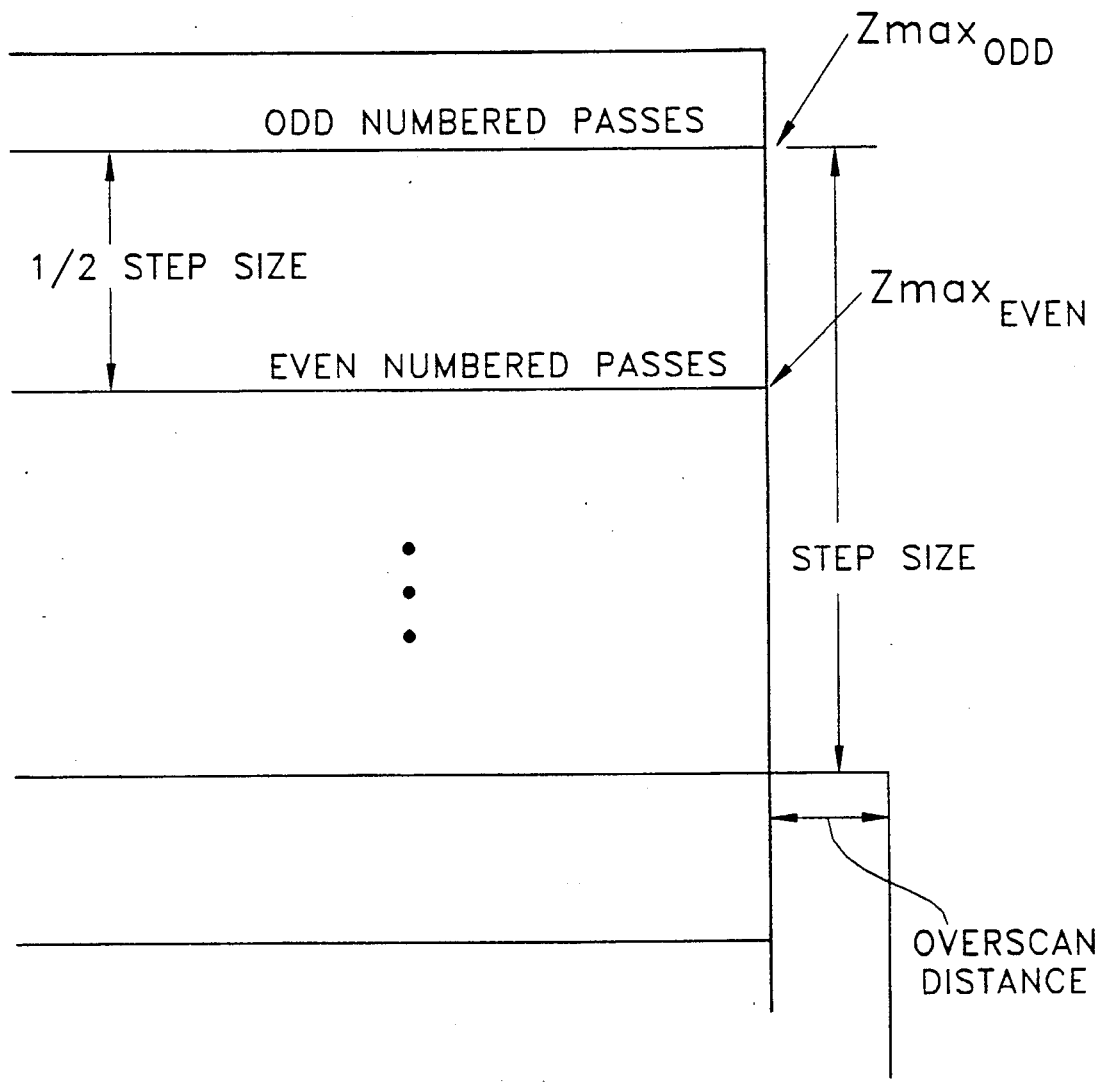
FIG. 8 is an expanded view of that portion of the raster scan pattern in FIG. 7A circled by the dotted line 8—8.

The current, voltage and magnetic waveforms shown in FIGS. 6A and 6B produce a scan pattern 150 as shown in FIG. 7A. It is again noted that these voltage and current waveforms, and the scan pattern 150, are only exemplary, as almost any desired scan pattern could be achieved by application of an appropriate current waveform to each magnet coil. However, as indicated in FIG. 7A, the preferred scan pattern 150, for a first pass, proceeds from a $Z_{max}$ coordinate location to a $Z_{min}$ coordinate location while scanning back and forth in the X coordinate direction. To begin a second pass, as might be desired in order to uniformly expose the target area to the scanning beam, especially to uniformly expose the unexposed target areas remaining between adjacent scan lines in the positive and negative X-directions, the scan pattern returns to the $Z_{max}$ coordinate location, except that for this second pass the slow magnet coil current is offset a prescribed amount, e.g. 8.5 amperes, (i.e., the $Z_{max-odd}$ coordinate is decreased to a $Z_{max-even}$ coordinate in order to position the starting point of the second pass just below the first pass, as shown best in the expanded view of the scan pattern shown in FIG. 8. Similarly, on returning for a third pass, another offset adjustment is made to position the beginning of a third pass to the same $Z_{max-odd}$ coordinate as the first pass. This process continues for as many passes as are required to uniformly expose the target area between each step size. A representative step size, measured in terms of the step current change in the slow scan magnet current, as indicated in FIG. 8, is 17 amperes. The step sizes are input in distance units (usually 1 cm). The raster control software calculates the necessary current step needed to achieve the desired distance step based on the beam particle and energy and the field-current relationship of the magnets.

The number of passes in the scan pattern that are required in order to uniformly expose the target area is governed by the step size and the beam spot size. For some applications, it may be desired, in order to provide a needed level of dose from the proton (or other charged-particle) beam, to scan the same target area more than once. Dose uniformity is likewise determined largely by beam spot size, as well as the scan rate. The beam spot size is a function of beam energy and the presence or absence of ridge filters in a collimator device that may be included within the nozzle structure of the beam delivery system. (The construction and use of collimator device, with or without ridge filters, is known in the art.) Advantageously, for a given beam energy (a known parameter that is either selected by the host processor 94 or provided from the system processor 92), the treatment room host processor 94 (FIG. 4) can readily be programmed by those skilled in the art to calculate the amount of over scan needed, if any, as well as to set the proper starting and ending points for each scan. The beam should be directed off the target area and onto the target collimator when it makes the slow magnet step. The distance away from the target area edge where the slow step is made is the overscan distance shown in FIG. 8. This distance ensures that only a negligible amount of beam will hit the target during slow steps and thus improve the dose uniformity.

The length of the scan depends in large part on the speed at which the fast and slow magnets sweep the beam across the target area. The configuration shown in FIG. 5 is designed to provide enough power to sweep the beam across the target area at speeds of up to 2400 cm/sec for the fast magnet and 333 cm/sec for the slow magnet for the stiffest (highest energy) beam of 250 MeV. At these fastest rates, it is preferred that only one magnet be allowed to sweep at any given time due to the high power required for changing the magnet currents. However, if lower energy (less stiff) beams are used, e.g., 50 MeV, then moderate sweep rates may be employed wherein sufficient power exists to allow both magnets to sweep simultaneously.

Figure 7B:
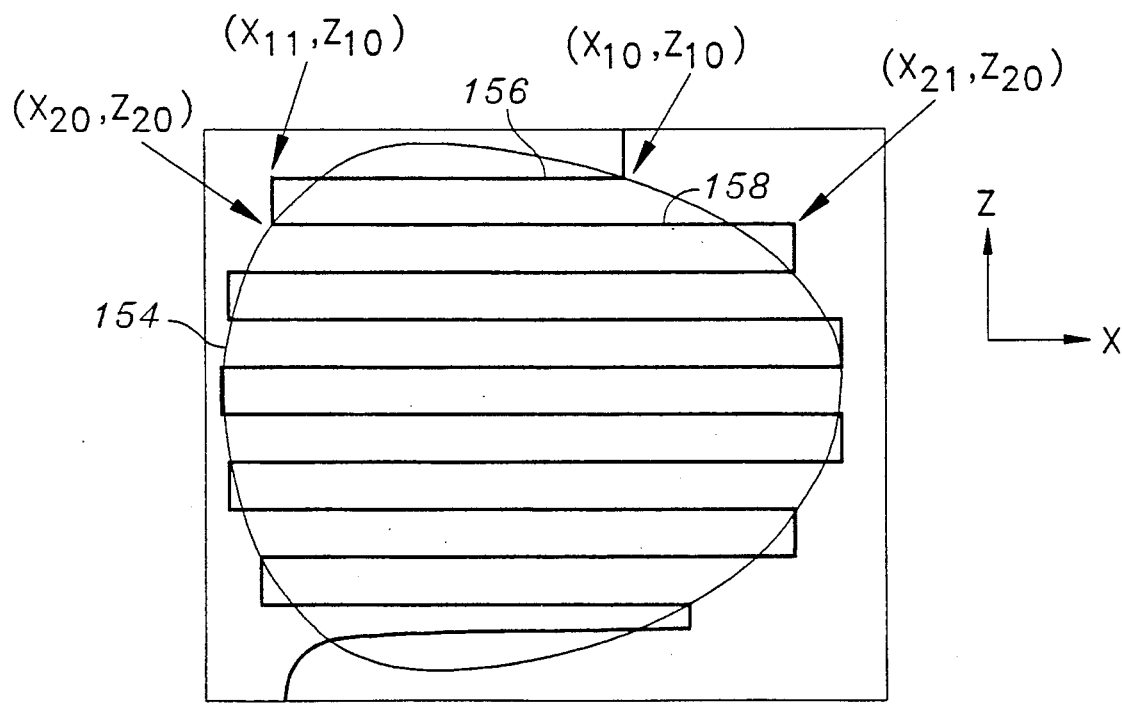

Referring to FIG. 7B, a preferred scan pattern for an irregular shaped target 154 is illustrated. In general, the pattern used for an irregular shaped target is much the same as for a rectangular shaped target (FIG. 7A). That is, the beam is moved to a $Z_{max}$ position, scanned in an X-direction, stepped down to a slightly lower Z position, scanned in the opposite X-direction, stepped down to yet a lower Z position, scanned in the X-direction, and so forth. The main difference between scanning an irregular shaped target 154 and a regular shaped target 32 lies in the fact that the start and end points of each scan line for an irregular shaped target may be different, while for a regular shaped target they are the same. That is, referring to FIG. 7B, the start point for a first scan line 156 (with reference to the X-Z coordinate system shown) may be identified as $(X_{10}, Z_{10})$; while the end point for the first scan line may be identified as $(X_{11}, Z_{10})$ During the scan of this first line 156, the current in the fast scan magnet is ramped in an appropriate direction in order to cause the fast magnetic field to sweep in the X direction from right to left, i.e., from the X-coordinate $X_{10}$ to the X-coordinate $X_{11}$, at the same time that the current in the slow scan magnet is held constant in order to cause the slow magnetic field to be held at a constant Z-coordinate $Z_{10}$. At the conclusion of the first scan line 156, i.e., when the desired end point $(X_{11}, Z_{10})$ is reached, the current in both the fast scan magnet and the slow scan magnet is adjusted as required in order to move the beam to the start point $(X_{20}, Z_{20})$ of a second scan line 158. As suggested in FIG. 7B, the first scan line end point may be the same as the second scan line start point, thereby necessitating only one magnet to change at any given time (thereby reducing power consumption). However, it is to be emphasized, that the present invention contemplates the ability to define the start and stop points of each scan line as needed. Assuming that sufficient power is available for operation of the fast and slow magnets, any desired scan pattern can be obtained on the target area, including very complex scan patterns.

Returning to FIG. 7B, during the scan of the second line 158, the current in the fast scan magnet is ramped in the opposite direction as was used in scanning the first scan line 156 in order to sweep the fast magnetic field from left to right, i.e., from the start point $(X_{20}, Z_{20})$ of the second scan line 158 to a desired end point thereof at $(X_{21}, Z_{20})$ This process continues for each scan line of the irregular shaped target, with each scan line having a start point ($X_{n0}$, $Z_{n0}$) and an end point ($X_{n1}$, $Z_{n0}$), where n is an integer and represents the nth scan line. Second, third, or more passes of the scan pattern can be achieved with the irregular shaped target of FIG. 7B in the same manner as used for the regular shaped target of FIGS. 7A and 8.

Advantageously, the start and end points of each scan line can be readily programmed into the raster control system by the treatment room host computer 94, thereby allowing any desired irregular shaped target area to be uniformly scanned with the charged-particle beam. For example, the host computer may be programmed, in conventional manner, to convert these programmed start and end points to equivalent time periods, given the sweep rates for each magnet that it is using, in order to determine when the current delivered to the appropriate magnet coil needs to be switched, stepped, or otherwise changed. Such changes are effectuated by generating an appropriately shaped raster scan current waveform signal 216 or 218 (FIG. 5) that is presented as an "input" signal to the respective power amplifiers. Once the desired input signal is received, the current and magnetic feedback loops operate as above described in order to ensure that the needed current waveforms and magnetic fields are generated to cause the beam to follow the specified scan pattern.

Included within the software that controls the raster system as described above is a tolerance monitor process. It is the function of the tolerance monitor process to rapidly steer the beam 24 away from the target area 32 to an appropriate shield 102 in the event that certain out-of-tolerance conditions are sensed. Such conditions include either a current or magnetic field amplitude error signal that exceeds a prescribed threshold. In this way, an automatic built-in safety mechanism is provided within the raster scan system that prevents the system from delivering a beam in an unsafe manner. This assumes, of course, that the other systems, e.g., the host computer 94 and/or the system processor 92, have also been programmed to do something that is safe to do in the event of a failure. Typically, the response taken by the raster scan system upon sensing an out-of-tolerance position is to saturate the power amplifiers in one direction or the other, thereby sending a maximum current into both magnet coils, which maximum current creates magnetic fields that steer the beam 24 into the shield 102. Once such an action has been taken, which may be thought of as a fail-safe state of the system, a reset command must be received in order to allow normal operation of the system to resume.

As has been indicated, the shield 102 (FIG. 4) may be the edge of a suitable collimator device used with the nozzle structure of a beam delivery system. It should be noted that merely turning off or shutting down the power amplifiers 212 and 214 in the event an out-of-tolerance condition is sensed would generally not be sufficient to prevent the beam from being delivered to the target, i.e., from preventing an unsafe condition. This is because the beam 24 is usually directed to strike the target with or without the presence of the magnetic fields 205 and/or 209. Thus, the preferred immediate response must be to steer the beam away from the target and let it strike a benign element, such as the shield 102. A long term response would typically include shutting the beam 24 off, which could be done either by blocking the beam at an appropriate location upstream from the nozzle, or simply turning the beam off (both of which typically require some time, e.g. several seconds, to finalize).

Figure 9:
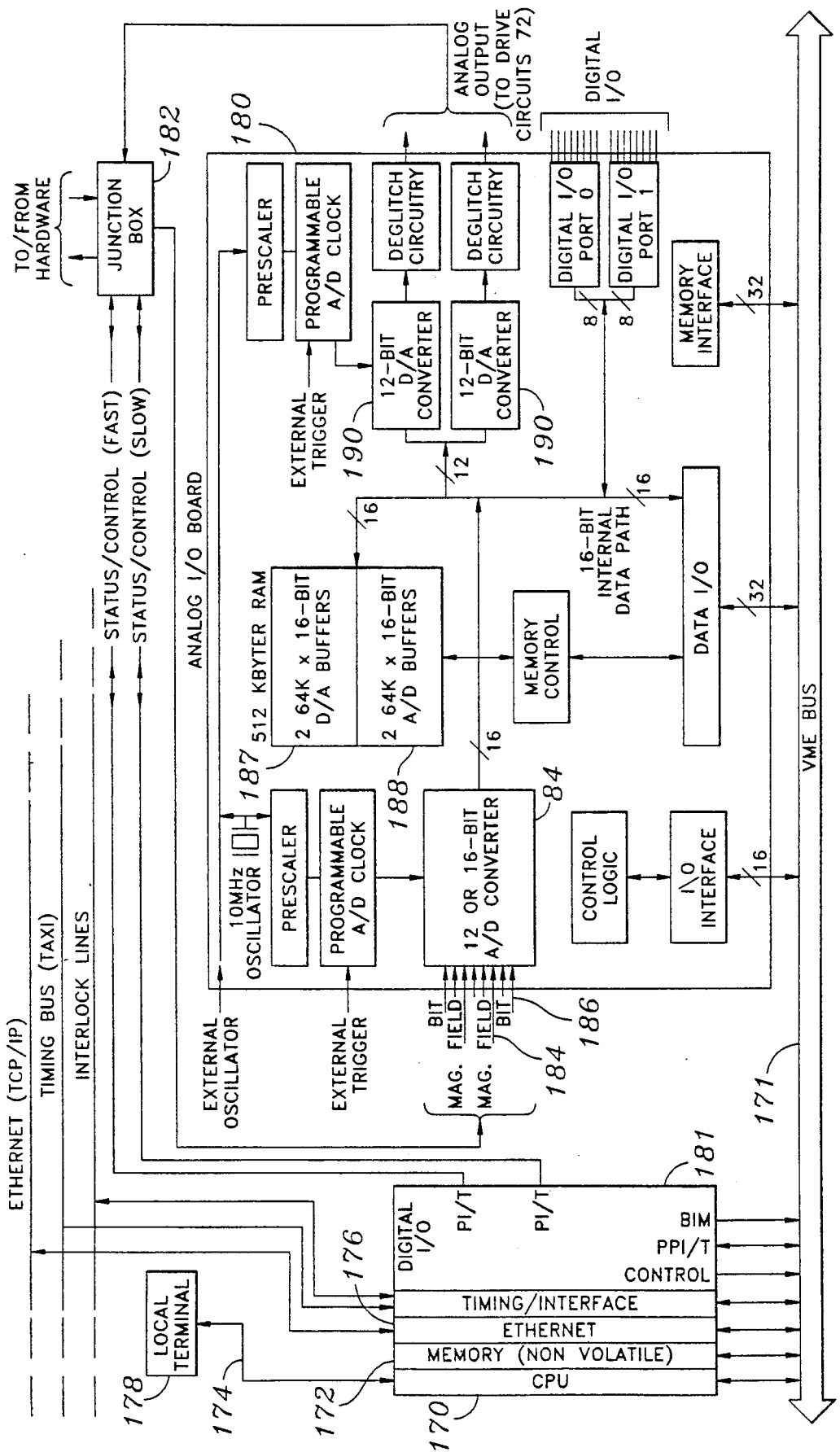
FIG. 9 is a block diagram of the raster scan signal generator used by the system of the present invention.

Referring next to FIG. 9, a block diagram of the raster scan generator circuitry 80 is shown. This generator includes as its main component a central processing unit (CPU) 170. A memory device 172 is coupled to the CPU 170 via a VME Bus 171, and provides storage locations where both the operating programs and control parameters associated with the raster scan system can be programmably stored. An RS-232 interface 174 provides an appropriate connection between a suitable local terminal (keyboard and monitor) 178. The terminal 178 is not needed for operation of the beam system, but may be optionally used for diagnostic and testing purposes. A communication network interface comprises a conventional Ethernet board 176. The software implementation uses TCP/IP compatible messages and Berkley BSD 4.3 sockets to communicate with the host computer. Various external commands, such as a prepare to sweep command and a start sweep command may be generated external to the CPU 170 by the operator, or by other external systems. Similarly, a system interlock command is likewise generated external to the CPU 170, by (for example) the system processor 92.

The interface circuits that send signals to and from the drive circuits 72 (and other hardware elements of the raster control system) and the CPU 170 are contained on an analog I/O board 180 or a digital I/O board 181. These interfacing signals are routed through a junction box 182. The analog-to-digital (A/D) interface between the analog signals of the drive circuits 72 and the digital operation of the CPU 170 is provided by A/D converter 84 and A/D buffer 187. These analog signals include the magnetic field feedback signal 184 for each of the fast and slow scan magnets, and built-in-test (BIT) signals 186 for each of the fast and slow scan power drive amplifiers.

The digital-to-analog (D/A) interface between the digital CPU 170 and the drive circuits 72 is provided through a buffer memory 188 and a D/A converters 190, connected to the buffer memory 188. These output signals include the raster scan input signals 216 and 218 for both the fast and slow drive amplifiers 212 and 214. Advantageously, any of the analog signals delivered to or received from the drive circuits 72 may be monitored at appropriate connectors at the junction box 182 using an appropriate monitoring device, such as an oscilloscope, as desired. These monitored signals include the raster scan signals 216 or 218, which signals define the desired magnetic field waveform that is to be generated.

The control and operation of the raster scan control system of the present invention is best described with reference to a Finite State Machine (FSM) model. Such models are extremely useful to reliably control complicated hardware. Such models are further useful in that they fully define the control and operation of the system in question, while allowing the detailed designer a great deal of flexibility in how the system is actually implemented. That is, because there exists a great many equivalent design choices that can be implemented, either in hardware, software, or a combinations of hardware and software, a description of the system in terms of an FSM model allows any of such equivalent design implementations to be selected. In other words, an FSM model, which includes a definition of the states associated with such a model, and the events that cause the system to switch from one state to another, clearly defines the operation of the system and enables one skilled in the art to readily implement the specified system, using any software, hardware, or combinations of hardware and software of his or her choice. Because of the advantages of using an FSM model, the Raster Generator 80 is shown in FIG. 4 as including state logic and control circuits 82.

In such a FSM model, it is noted that events happen at specific moments in time, while states endure through extended periods of time. Events can be externally generated, or can be internally generated by the system. An event is required to cause a state transition, i.e., to switch the system from one state to another. As each state is entered, appropriate commands are generated to cause prescribed actions to happen, e.g., to cause the hardware to respond in a certain fashion. Events are classified as real time or non real time. Those which are real time require fast response and thus are usually implemented as timing or other hardwired signals. The non-real time events may be passed to the system over the computer network as messages. These message events may contain additional information beyond the events occurrence.

Hardware events are either transitions between states of the hardware signal lines or timing events decoded in appropriate decoding logic. An on-to-off line transition may be a different event than an off-to-on line transition of the same signal. Hardware signal line levels are tested when transitions occur as part of the state of the system, and thus help to determine the next state.

Figure 10:
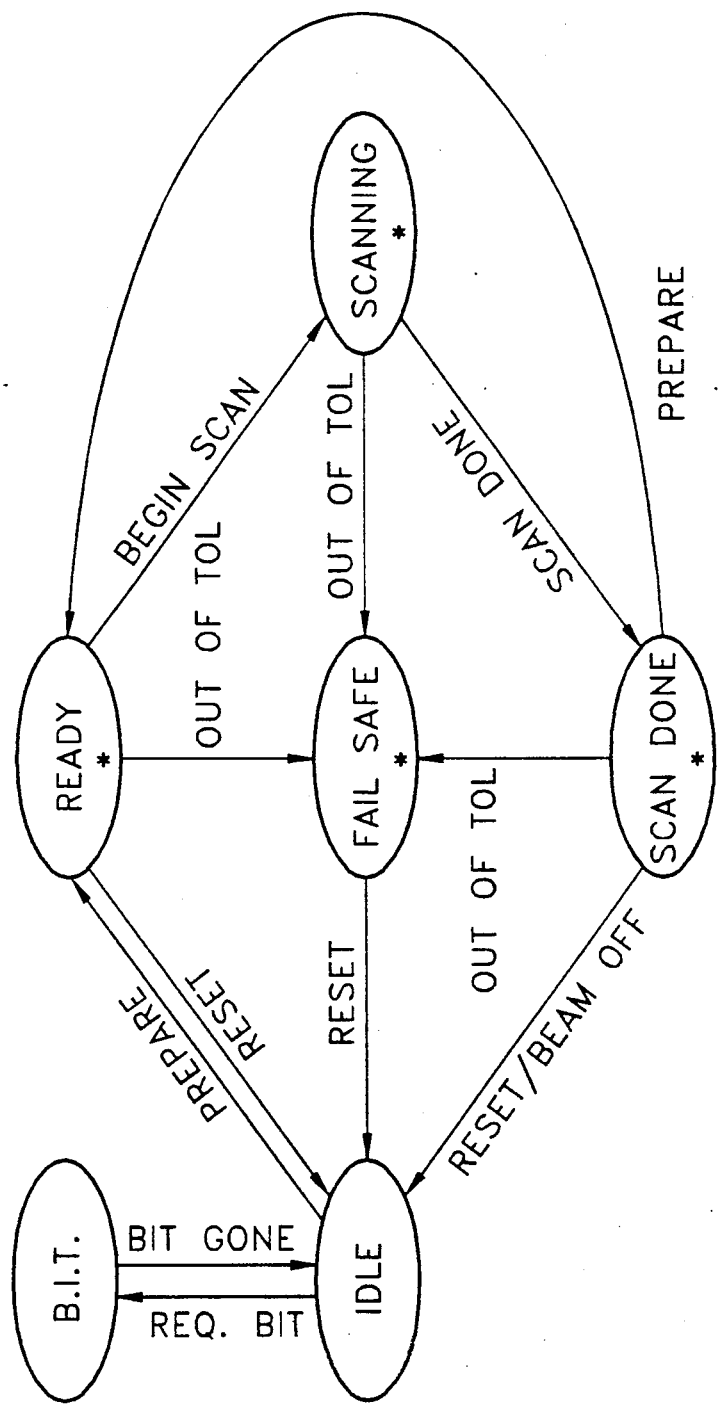
FIG. 10 is a state logic diagram illustrating the various operating states of the raster scan system of the present invention and the type of event(s) that cause the system to change from one state to another.

The FSM model of the charged-particle raster scan control system of the present invention includes just six states: (0) Idle; (1) Doing Built-In-Test (BIT); (2) Ready; (3) Scanning; (4) Scan Done; and (5) Fail Safe. Further, there are just nine events that can happen within the system: (0) Request Status; (1) Request BIT; (2) BIT Done; (3) Prepare for Beam; (4) Begin Scan; (5) Scan Done; (6) Beam Off; (7) Field Out of Tolerance; and (8) Reset. A graphic representation of this FSM model is shown in FIG. 10.

It is noted that six of the nine events are external events, namely Request Status, Request BIT, Prepare for Beam, Begin Scan, Beam Off, and Reset. These events are all message events except for Begin Scan and Beam Off which are timing signals. The remaining three events—BIT done, Scan Done, and Field Out of Tolerance—are internally generated by the raster scan control system.

Naturally, there are some signals that the control system internally generates and which are passed to the "outside" world, primarily to the system processor 92 or the treatment room host 94. In general, these are error messages sent over the network 96 or hardware interlock signals (such as ready for beam or abort beam) sent via appropriate alternate signal lines.

A description of each of the six states of the system is as follows:

The Idle state is the state where power is off to the scanning magnets, and the system is ready to accept commands.

The Doing BIT state is the state where the system is performing a Built-In-Test. The BIT includes generating an appropriate raster scan signal (116 or 118) and feeding it back into the CPU 170 for analysis to verify that it has been generated correctly. The system returns to the Idle state when the BIT is completed.

The Ready state exists when the system has received and verified the treatment (target) field information. In this state, the magnetic fields are sweeping any potential beam off the treatment area onto the collimator edge (shield 102). When this state is entered, the beam inhibit interlock signal 90 (FIG. 5) is removed.

The Scanning state exists when a treatment scanning pattern is in progress. This is the only state in which the beam is directed at the target or treatment area.

The Scan Done state exists when a scan pattern has been completed and the system is awaiting a beam off event. In this state, the magnetic fields are sweeping any potential beam off the target site onto the shield or equivalent device.

The Fail Safe state exists when an out-of-tolerance condition relative to the magnetic field has been sensed during a time while the scanning magnets are energized. In this state, both the fast and slow magnets are energized and direct the beam into the shield or equivalent device (collimators).

A description of the nine events that cause the system to switch from one state to another state is next presented. This description is best understood with reference to FIG. 10.

Request Status is an external event or message that is transmitted to the raster scan control system of the present invention to request the status (state, etc.) of the system. This event may occur at any time. Several versions of this event (request) exist. The smallest request returns only the state of the system. A second type of request provides a playback of the treatment field setup information. A third type of request dumps the scan position feedback values for the last scan. This dump preferably includes a flag to indicate if this last scan terminated abnormally. This is a network message event, meaning that the request is made, and the response given, over the ethernet communications network 96.

Request BIT event is a request that the Built-In-Test be run. This request may only be made while the system is in the idle state. When received, and if the system is in the Idle state, the system switches to the BIT State. This is also a network message event.

BIT Done is an event that signals the built-in-test, as requested by the Request BIT event, has been completed. This event is internally generated by the system. It causes the system to switch from the BIT state back to the Idle state.

Prepare for Beam ("Prepare") is a network message event received over the ethernet communications network that contains the treatment field (target area) information. Once this information has been received and verified, the system changes from the Idle state to the Ready state. In Ready state, the magnets are energized to a standby position which moves the beam off of the treatment area. Usually, even though the beam is not on the target area, the fields are still sweeping the potential beam back and forth across the shield (e.g., edge of the collimator) in order to prevent the shield from receiving all the unused dose in one location or spot. In the Ready state, the slow magnet is fixed and the fast magnet is sweeping.

Begin Scan is a hardware signal or event that occurs at a fixed time, roughly 25 msec before the raster scanning of the beam is to begin. This provides the system sufficient time to bring the fields to the start of the treatment position (starting coordinates). As seen in FIG. 10, this event causes the system to change from the Ready state to the Scanning State. Scanning of the target area begins without further events happening. The begin scan event should not occur within approximately 75 msec of the Prepare event in order to provide sufficient time for the magnets to move their fields to their standby positions, i.e., to allow the system to be fully ready and enter the Ready state.

Scan Done is an internal event that occurs when the scanning of the target area, as specified in the Prepare of Scan message, has been completed. This event causes the system to switch from the Scanning state to the Scan Done state. During the Scan Done state, power is still applied to the scanning magnets, but the beam is moved off of the target area onto the shield area.

Beam Off is an event that serves as a reset signal. It is a hardware timing signal that occurs at or after the end of the beam dump, i.e., at the end of an allotted time during which the beam should have completed its programmed scan pattern and the specified beam dose should have been delivered. It causes the system to change from the Scan Done state to the Idle State and to de-energize the magnets.

Field Out of Tolerance is an internal event that may occur anytime while power is applied to the scanning magnets and an out of tolerance condition relative to the magnetic fields is sensed. It causes the system to automatically switch from whatever state it is in (Ready, Scanning, or Scan Done) to the Fail Safe state and move the beam off the target area to a safe position on the collimator.

Reset is an event that returns the system to the Idle state from any state except the Scanning State. This is a network message event. This event is the only way that the system can leave the Fail-Safe state.

As has been indicated, the system of the present invention cannot control when external events may happen. Thus, the system is designed to respond to any external event while in any state. The action of the system when any event happens is defined below in Table I, which is a state transition table. The "Notes" following the table explain the symbols used therein.

communication networks are well documented in the art, and their use is widespread. Any suitable format and communication protocol could be used to send messages to and from the treatment room host computer. Such communications may be accompanied by a timing system, an interlock system, or other external systems, as desired. Such systems may be included as part of the system processor 92 or the treatment room host computer 94.

In the preferred embodiment, the four external network messages (Request Status, Request BIT, Prepare, and Reset) are communicated over the ethernet communications network using a TCP/IP protocol, which protocol is well documented in the art. In general, the preferred format contains a message identifier followed by message dependent data. Each message generates a reply that signals either success (ACK) or failure (NAK), followed by message dependent data.

For example, the format for a "Prepare for Beam" message may take the following format:
Prepare for Beam (message identifier)
Beam Energy (message dependent data, or MDD)
Confirm Fast Magnet Speed (MDD)
Confirm Slow Magnet Speed (MDD)
Number of Scans (MDD)
Number of Lines per Scan (MDD)
Start/Stop Coordinates (MDD)
Check Value (MDD)
Prepare for Beam Reply (message identifier)
ACK or NAK (MDD)
Check Value (MDD)

Advantageously, the majority of the components used within the raster scan system of the present invention are commercially available. For example, as has been indicated, the fast scan power amplifier 112 may be realized using a Model 290 power amplifier available from Copley Controls Corporation of Newton, Mass. The slow scan power amplifier 214 may be realized

TABLE I

| External Events | State Transition | | | | | |
| --- | --- | --- | --- | --- | --- | --- |
| | 0 Idle | 1 Doing BIT | 2 Ready | 3 Scanning | 4 ScanDone | 5 FailSafe |
| Request Status | a | a | a | a | a | a |
| Request BIT | b/1 | e | e | e | e | e |
| Prepare | cd ↑/2 | fcd ↑/2 | ↓c↑ | e | ↓c↑/2 | e |
| Begin Scan | e | e | lk/3 | e | e | e |
| Beam-Off | i | i | e↓m/0 | ↓m/0 | ↓m/0 | i |
| Reset | /0 | /0 | ↓m/0 | i | ↓m/0 | m/0 |
| Internal Events | | | | | | |
| BIT done | | /0 | | | | |
| Scan done | | | | ↓/4 | | |
| Field OT* | | | ↓h/5 | ↓/5 | ↓/5 | |

*OT = out of tolerance (the sweep field measurements do not agree with requested values to within the allowed tolerance)
Note Action
a Generate status message (contents depends on state and type of request)
b Start built in test
c Receive/check information, if ok send ready status with check data; else send error
d Energize magnets to stand-by position. 75 milliseconds must pass before the system is ready for a begin scan event (time required to get to stand-by position)
e Error! Send error message with state and event causing error
f Stop doing BIT
h Send magnets to fail safe position
i Ignore event
k Start the target area scan
l Wait until 25 minutes have passed since the Beam Good signal
m De-energize magnets
t Send set time-out error message; send ready status message
↑ Turn on ready-for-beam hardware interlock line (enable beam)
↓ Turn off ready-for-beam hardware interlock line (inhibit beam)

As indicated in FIG. 4, the system of the present invention communicates with the treatment room host 94 via an ethernet communications network 96. Such using two Model 290 power amplifiers connected in parallel master-slave configuration. The current sensors 222 and 230 may be a Model 310 sensor, also available from Copely Controls Corporation; and the magnetic field probes 204 and 208 may be a suitable Hall effect device, such as the Model MG-2AB gauss-meter manufactured by Walker Scientific Inc. and the associated Hall effect probe and cable Model HP-32R-10 also manufactured by Walker Scientific. The CPU 170 included in the raster scan generator 80 may be a single board computer, Model MV-133 available from Motorola Corporation of Tempe, Ariz. The memory 172 may be any of several memory cards or systems available, or easily assembled, using commercially available memory chips. The preferred memory capacity is 1 Mbit of non-volatile RAM. The Ethernet network is a commercially available local area network (LAN) system available from Motorola and other vendors. The A/D and D/A converters are commercially available devices, Models DT 1492-8DI, available from Data Translation of Marlboro, Mass. The power supply 74 may be provided from any suitable power supply vendor, such as DynaPower Corporation. Those components that may not be available commercially can readily be fashioned by those skilled in the art given the descriptions and specifications presented herein using commercially available components, such as commonly available logic gates, registers, operational amplifiers, and the like.

Figure 11:
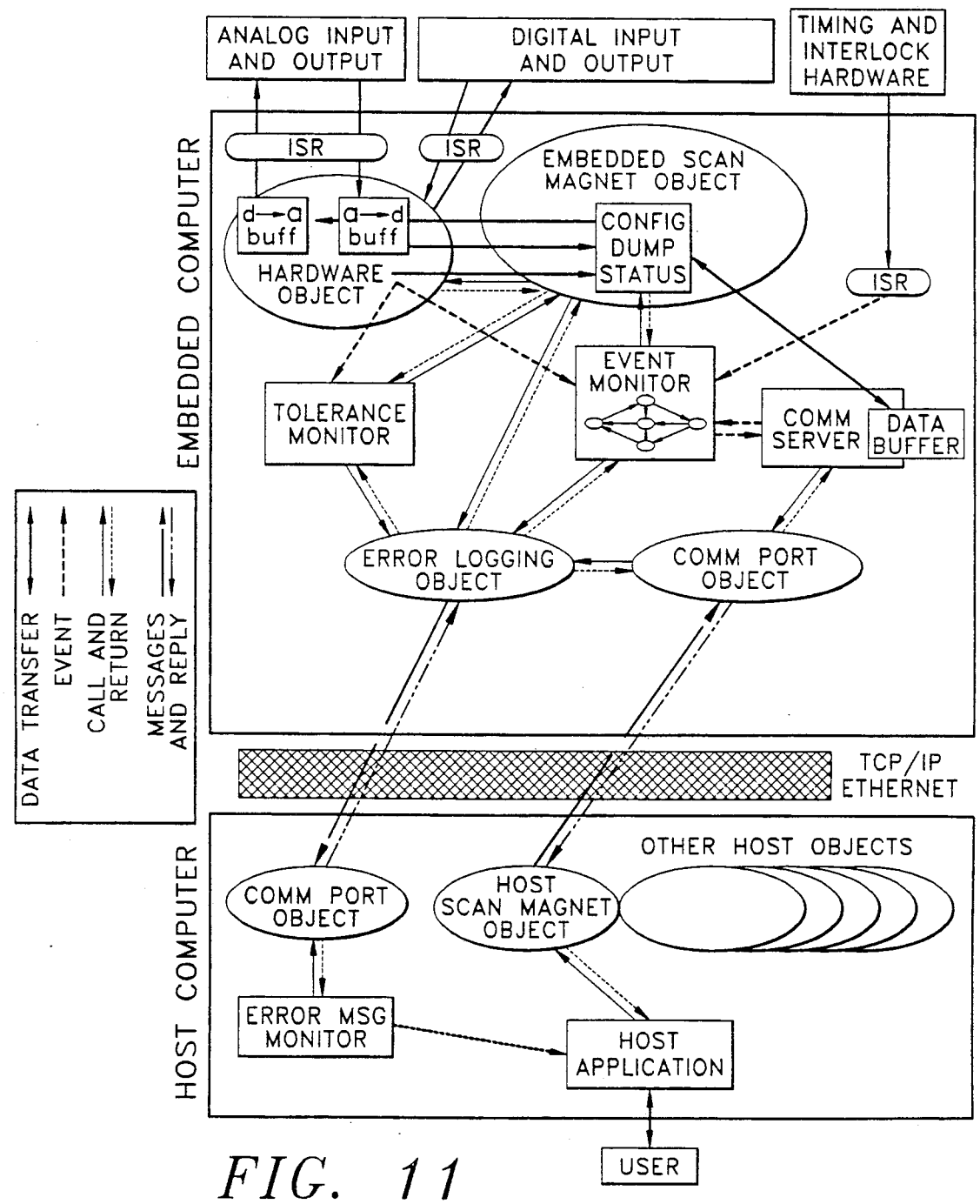
FIG. 11 is a software module diagram illustrating the interconnections of the various processes that combine to provide control of the raster scanning hardware.

Referring next to FIG. 11, a representation of the software used to control the raster scan magnets is shown. The software depends on several concurrently running processes (depicted as rectangular boxes) and interrupt service routines (ISR's) to handle the hardware and software control requirements. The software design philosophy is based on an object oriented approach that has been shown to produce stable, yet easily modifiable, maintainable and debuggable code. The objects are depicted as ovals in FIG. 11. Each object is a collection of private data structures and publicly callable methods (i.e., subroutines) that operate on those data structures. The software uses event flags to pass signals from one process to another, and messages for communicating between processes residing on different computers. The inter-computer communication is based on a server-client model where the client process opens a communication path to a server who then responds to the client's requests.

In the current implementation, the embedded raster scan computer has a server that responds to requests from the host computer. There is also an error message server on the host that responds to error messages generated asynchronously by the embedded systems. Error messages generated synchronously (i.e., as a result of a specific request) are handled by replying with a NAK failure code.

Figure 12:
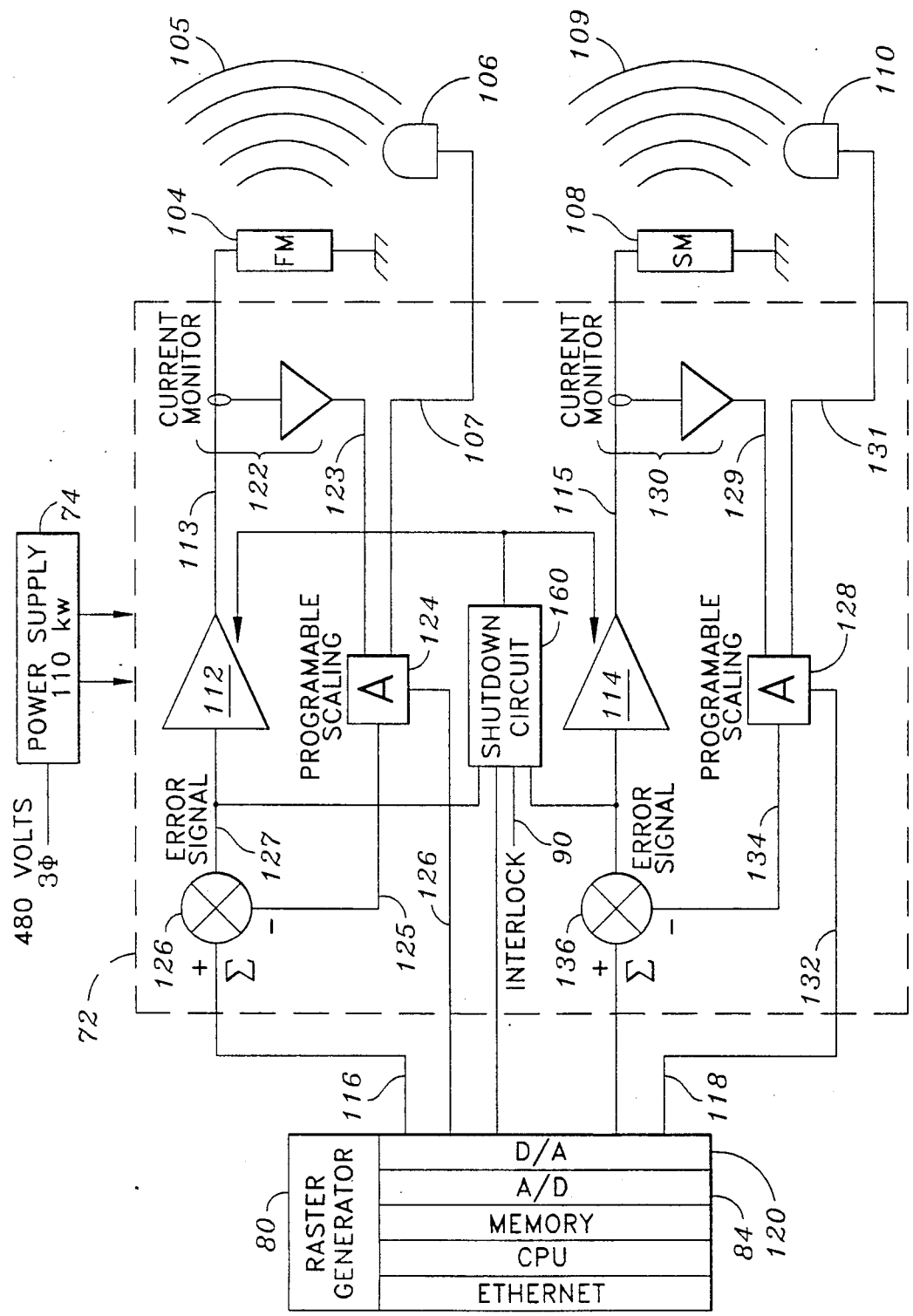
FIG. 12 is a block diagram of an alternative embodiment of the raster scan control circuits of the present invention wherein both the coil current and magnetic field values may be used as feedback signals to control the magnetic fields generated by each electromagnet.

Turning next to FIG. 12, an alternative embodiment of the power drive circuits 72 of the raster scan system 68 of FIG. 4 is illustrated. As seen in FIG. 12, this alternate embodiment includes a fast scan magnet (or "fast magnet") 104 and a slow scan magnet (or "slow magnet") 108, similar to the prior art (FIG. 2). Like the prior art devices, each magnet includes a magnet coil. When the magnet coil of each magnet is energized by an electrical current, a fast magnetic field 105 (fast magnet) and a slow magnetic field 109 (slow magnet) is generated. (These magnetic fields are represented in FIG. 12 by a series of radiating wavefront lines emerging from their respective magnets.) Unlike the prior art, however, a fast magnetic field probe 106, and a slow magnetic field probe 110, sense the instantaneous strength of the respective magnetic fields 105 and 109. This sensing allows the drive circuits, as will be explained hereafter, to make adjustments in the electrical currents creating the magnetic fields so that the magnitudes and polarities of such magnetic fields can be dynamically forced to follow a desired waveform.

Further, unlike the prior art, each magnet 104 and 108 is driven by a power amplifier 112 and 114, respectively. These power amplifiers generate the large currents 113 and 115 ("output currents") used to drive the fast magnet 104 and the slow magnet 108 as controlled by respective raster control signals 116 and 118, obtained from a digital-to-analog (D/A) portion 120 of the raster generator 80. As with FIG. 5, these raster control signals 116 and 118 may be considered as the raw "input" signals to the power amplifier circuits 112 and 114, for it is these signals that define the desired current waveform that the large currents generated by the power amplifiers 112 and 114 are to take, and hence the waveform that the amplitude of the magnetic fields 105 and 109 are to follow.

The raw input signals 116 and 118 are modified, as necessary, in order to correct for any deficiencies that may exist in either the output currents 113 or 115, or the magnetic fields 105 and 109. This modification is achieved using, in effect, separate current and magnetic feedback loops. However, these "separate" feedback loops may be combined to operate, in effect, as a single feedback loop. The fast magnet feedback loop includes the magnetic probe 106, which probe 106 generates a signal 107 indicative of the instantaneous strength of the magnetic field 105; and a current monitor 122, which monitor generates a signal 123 indicative of the instantaneous magnitude of the current 113. Both the probe signal 107 and the current signal 123 are connected to a programmable scaler circuit 124. It is the function of the scaler circuit 124 to receive the signals 107 and 123 and scale (adjust) them as controlled by a programmable signal 126 received from the D/A 120 or the raster generator 80. (This scaling may be thought of as a weighting process, i.e., the signal 126 instructs the scaler circuit 124 how much weight should be given to the current monitor signal 123 and to the field probe monitor signal 107.) The scaler circuit 124 generates an appropriate scaled feedback signal 125 that is presented to an appropriate summing point 126. At the summing point 126, the scaled feedback signal 125 is, in effect, compared with the raw input signal 116. This comparison typically takes the form of subtracting the feedback signal 125 from the input signal 116, hence, the feedback signal is shown in FIG. 5 as being applied to the summing point 126 with a negative sign "−", while the input signal is applied to the summing point with a positive sign "+". The difference between these two signals is an "error signal" 127, representing how much error there is between the actual measured output parameter (the current 113 and/or the magnetic field 105), which error signal is then applied to the amplifier 112 as a direct input signal that adjusts the output current 113 in a direction that minimizes the error.

To explain further the operation of the scaler circuit 124, and the relationship between the two feedback loops that are employed (one for the current 113 and the other for the magnetic field 105) it is noted that, at any given time, the scaler circuit 124 may be instructed to give zero weight to the current signal 123 and 100% weight to the field signal 107. In such a situation, the magnetic field signal 107 is essentially providing the sole feedback signal. Alternatively, the scaler circuit 124 may be instructed to give zero weight to the field signal 107 and 100% weight to the current signal 123, in which case the current signal 123 provides the sole feedback signal. Typically, however, the scaler circuit 124 is instructed to provide some weight to the current signal 123 and some weight to the magnetic field signal 107, resulting in the feedback signal 125 being a combination of the two signals 123 and 107. For example, the feedback signal 125 may be weighted so as to comprise 20% of the current signal 123 and 80% of the magnetic field signal 107, in which case the magnetic field signal dominates the feedback signal, but does not control it entirely.

The slow scan feedback loop includes the same elements as does the fast scan feedback loop, described above, and operates in the same fashion. That is, a slow magnet scaler circuit 128 receives a signal 129 from a current sensor 130 that indicates the amplitude of the current 115. It also receives a signal 131 that indicates the instantaneous magnitude or strength of the magnetic field 109 as sensed by the probe 110. A control signal 132 received from the raster generator 80 instructs the scaler circuit 128 how much weight is to be given each of these signals in a slow magnet feedback signal 134 that is compared to the desired raw input signal 118 at a summing point 136. Based on this comparison, a slow magnet error signal 138 is generated that is presented to the power amplifier 114 in order to automatically adjust the output current 115 in a direction that minimizes the error.

While the invention herein disclosed has been described by means of specific embodiments and applications thereof, numerous modifications and variations could be made thereto by those skilled in the art without departing from the spirit and scope thereof. Accordingly, it is therefore to be understood that within the scope of the appended claims, the invention may be practiced otherwise than as specifically described herein.

What is claimed is:

1. A system that scans a target area with a charged-particle beam comprising:
   means for generating a charged-particle beam having a described energy;
   means for directing said beam through a pair of magnets having orthogonally oriented magnetic fields, each magnet having a coil associated therewith;
   means for generating a sweeping magnetic field with a first of said magnets, said sweeping magnetic field causing said beam to sweep back and forth across the target area in one direction;
   means for generating a stair-stepped magnetic field with a second of said magnets, said stair-stepped magnetic field assuming a first magnetic field strength for a first prescribed period of time, a second magnetic field strength for a second prescribed period of time, a third magnetic field strength for a third prescribed period of time, and so on up to an nth field strength for an nth prescribed period of time, where n is an integer and represents the number of steps in said stair-stepped magnetic field, said stair-stepped magnetic field causing said beam to step across the target area in a direction orthogonal to the direction caused by said sweeping magnetic field; and
   means for synchronizing the sweeping magnetic field generating means with the stair-stepped magnetic field generating means so that the sweeping magnetic field begins its sweep coincident with the beginning of one of said prescribed periods of time during which the stair-stepped magnetic field has assumed one of its n magnetic field strengths;
   whereby said sweeping and stair-stepped magnetic fields combine to steer the beam across the target area in a desired raster scan pattern.

2. The system of claim 1 wherein each of said pair of orthogonal magnetic includes a coil and wherein said means for generating a sweeping magnetic field comprises means for energizing the coil of said first magnetic with a first current having an increasing amplitude, to sweep the magnetic field in one direction, and with a current having a decreasing amplitude, to sweep the magnetic field in the other direction.

3. The system of claim 2 wherein said first current having an increasing amplitude comprises a current having a linearly increasing amplitude and said current having a decreasing amplitude comprises a current having a linearly decreasing amplitude.

4. The system of claim 2 wherein said means for energizing the coil of said first magnet with said first current comprises:
   a first servo amplifier that produces said first current in response to a first input signal applied thereto;
   a raster signal generator for generating said first input signal; and
   means for programmably controlling said raster signal generator to cause said first input signal to assume a first waveform, said first waveform programmably controlling the sweeping magnetic field generated by said first magnet.

5. The system of claim 4 wherein said first servo amplifier further includes feedback means for monitoring the strength of the sweeping magnetic field and comparing the same to a first reference signal and for automatically adjusting the first input signal in order to force the magnetic field to assume the magnetic field strength defined by said first reference signal.

6. The system of claim 5 wherein said first servo amplifier further includes feedback means for monitoring the amplitude of the first current and comparing the same to a second reference signal and for automatically adjusting the first input signal in order to force the first current to assume the current amplitude defined by said second reference signal.

7. The system of claim 1 wherein each of said magnets includes a coil, and wherein said means for generating a stair-stepped magnetic field comprises means for energizing the coil of said second magnet with a second current having a stair-stepped waveform, said stair-stepped waveform causing said second current to assume a nth fixed value for each of said nth prescribed periods of time.

8. The system of claim 7 wherein said means for energizing the coil of said second magnet with said second current comprises:
   a second servo amplifier that produces said second current in response to a second input signal applied thereto;
   a raster signal generator for generating said second input signal; and
   means for programmably controlling said raster signal generator to cause said second input signal to assume a stair-stepped waveform, said stair-stepped waveform programmably controlling the stair-stepped magnetic field generated by said second magnet.

9. The system of claim 8 wherein said second servo amplifier further includes feedback means for monitoring the strength of the stair-stepped magnetic field and comparing the same to a first reference signal and for automatically adjusting the second input signal in order to force the magnetic field to assume the desired stair-stepped magnetic field strength defined by said first reference signal.

10. The system of claim 9 wherein said second servo amplifier further includes feedback means for monitoring the amplitude of the second current and comparing the same to a second reference signal and for automatically adjusting the second input signal in order to force the second current to assume the current amplitude defined by said second reference signal.

11. A method of scanning a target area with a charged-particle beam comprising the steps of:
    (a) generating a charged-article beam having a first energy;
    (b) directing said beam through a pair of magnets having orthogonally oriented magnetic fields, each magnet having a coil associated therewith;
    (c) generating a sweeping magnetic field with a first of said magnets by energizing its coil with a first current having an increasing amplitude to sweep the magnetic field in one direction and with a decreasing amplitude to sweep the magnetic field in the other direction, said sweeping magnetic field causing said beam to sweep back and forth across the target area in one direction;
    (d) generating a stair-stepped magnetic field with a second of said magnets by energizing its coil with a second current having a stair-stepped waveform, said stair-stepped waveform causing said second current to assume a first fixed value for a first prescribed period of time, stepping a prescribed amount to a second fixed value, assuming said second fixed value for a second-prescribed period of time, and so on, said stair-stepped magnetic field causing said beam to step across the target area in a direction orthogonal to the sweep direction; and
    (e) synchronizing the delivery of said first and second currents to the coils of said first and second magnets so that the first current is increasing in amplitude during the prescribed period of time when the second current assumes one of the fixed values in its stair-stepped waveform, and so that the first current is decreasing in amplitude during the next prescribed period of time when the second current assumes the next fixed value in its stair-stepped waveform;
    whereby said sweeping and stair-stepped magnetic fields combine to steer the beam across the target area following a controlled raster scan pattern.

12. The method of claim 11 wherein the fixed values of said stair-stepped current waveform are separated by a constant value increment.

13. The method of claim 11 wherein the step of generating a sweeping magnetic field comprises generating a linearly increasing or decreasing magnetic field by linearly ramping said first current from a first value to a second value.

14. A method of steering a charged-particle beam of a beam delivery system along a prescribed raster scan pattern at a target site lying in an X-Z plane, said beam delivery system including a nozzle through which the beam passes prior to reaching the target site, said nozzle including fast and slow scanning electromagnets positioned within said nozzle so as to create X-Z orthogonal magnetic fields therein, each of said magnetic fields interacting with said beam in a way that causes said beam to be deflected in an X or Z direction by an amount proportional to the strength of the magnetic field, said method comprising the steps of:
    (a) applying a first slow scan electrical current to the slow scan electromagnet and a first fast scan electrical current to the fast scan electromagnet, said first slow scan current creating a slow scan magnetic field that steers the beam in a Z direction on the target site to a desired $Z_{10}$ coordinate, and said first fast scan current creating a fast scan magnetic field that steers the beam in an X direction to a desired $X_{10}$ coordinate, said $X_{10}$ and $Z_{10}$ coordinates comprising a first sweep start point ($X_{10}$, $Z_{10}$);
    (b) maintaining the first slow scan current in the slow scan magnet for a first period of time;
    (c) ramping the electrical current in the fast scan electromagnet from said first fast scan electrical current to a second fast scan electrical current over said first period of time, said ramping of electrical current creating a sweeping fast scan magnetic field that steers the beam in an X direction from said first sweep start point ($X_{10}$, $Z_{10}$) to a first sweep end point ($X_{11}$, $Z_{10}$), said first sweep end point being a prescribed distance from said first sweep start point ($X_{11}$–$Z_{10}$), said prescribed distance being determined by the duration of said first period of time and the slope of said ramping electrical current;
    (d) altering the fast and slow scan electrical currents, as required, from the values existing at the end of said first period of time to whatever values are required to steer the beam from the first sweep end point ($X_{11}$, $Z_{10}$) to a second sweep start point ($X_{20}$, $Z_{20}$);
    (e) maintaining the value of current in the slow scan magnet existing after performing the previous step for a second period of time;
    (f) ramping the electrical current in the fast scan electromagnet from the value existing after reaching the most recent sweep start point to a new value over said second period of time, said ramping having a slope opposite that performed in the previous sweep, said new value being that value required to steer the beam from the second sweep start point ($X_{20}$, $Z_{20}$) to a second sweep end point ($X_{21}$, $Z_{20}$);
    (g) repeating steps (d) through (f), as required, incrementing the modifiers "first" to "second", "second" to "third", "third" to "fourth", and so on, in order to move the beam from an nth sweep end point ($X_{n1}$, $Z_{n10}$), where n is an integer, to the next sweep start point ($X_{(n+1)0}$, $Z_{(n+1)0}$), and from an (n+1)th sweep start point ($X_{(n+1)0}$, $Z_{(n+1)0}$) to the (n+1)th sweep end point ($X_{(n+1)1}$, $Z_{(n+1)1}$), until the target site has been covered by the respective sweeps of said beam.

15. The method of claim 14 wherein the altering of the slow scan electrical current in step (d) comprises stepping the slow scan current from its previous value to a new value in a fixed increment for each sweep.

16. A raster scan control system for a charged-particle beam delivery system providing precise control of large currents driving an inductive load, the beam delivery system comprising:

a nozzle through which a charged-particle beam passes prior to being directed to a target, the nozzle including fast and slow sweep scan electromagnets that cooperate to generate a sweeping magnetic field that steers the beam along a desired raster scan pattern at the target, the electromagnets being driven by large currents from a raster scan control system;

a raster scan control system including fast and slow power amplifiers for delivering the large currents to the fast and slow electromagnetics, respectively;

a programmable raster generator for providing the fast and slow power amplifiers with raster scan signals that define a desired raster pattern for the charged-particle beam;

monitoring means for monitoring the magnetic field generated by the electromagnets;

sensing means for sensing the large currents;

feedback means responsive to the monitoring means and the sensing means for controlling the magnetic field and large currents;

out of tolerance means for automatically causing the power amplifiers to steer the beam away from the target upon detection of an out of tolerance event in the system; and a power supply for delivering power to the power amplifiers.

* * * * *